US012700481B2

(12) United States Patent
Barve

(10) Patent No.: US 12,700,481 B2
(45) Date of Patent: Aug. 4, 2026

(54) APPARATUS AND METHOD FOR RESPONDING TO A USER QUERY BY GENERATING A DATA STRUCTURE

(71) Applicant: nference, Inc., Cambridge, MA (US)

(72) Inventor: Rakesh Barve, Bengaluru (IN)

(73) Assignee: nference, Inc., Cambridge, MA (US)

( * ) Notice: Subject to any disclaimer, the term of this patent is extended or adjusted under 35 U.S.C. 154(b) by 0 days.

(21) Appl. No.: 18/808,618

(22) Filed: Aug. 19, 2024

(65) Prior Publication Data

US 2026/0051375 A1     Feb. 19, 2026

(51) Int. Cl.
G16H 10/20          (2018.01)
G06F 16/18          (2019.01)
G16H 10/60          (2018.01)

(52) U.S. Cl.
CPC .........  G16H 10/20 (2018.01); G06F 16/1805 (2019.01); G16H 10/60 (2018.01)

(58) Field of Classification Search
CPC ..... G16H 10/20; G16H 10/60; G06F 16/1805
USPC ........................................................ 707/754
See application file for complete search history.

(56) References Cited

U.S. PATENT DOCUMENTS

| 2010/0145720 | A1 | 6/2010 | Reiner | |
| 2020/0098480 | A1 | 3/2020 | Markovic et al. | |
| 2021/0004714 | A1 * | 1/2021 | Neumann | G06N 5/02 |
| 2021/0090694 | A1 * | 3/2021 | Colley | G16H 50/50 |
| 2023/0335243 | A1 * | 10/2023 | Mukherjee | G06N 5/00 |
| 2024/0169714 | A1 * | 5/2024 | AlRegib | G16H 30/20 |
| 2025/0259041 | A1 * | 8/2025 | Crabtree | G06N 3/047 |

FOREIGN PATENT DOCUMENTS

IN          202311027839 A      5/2023

* cited by examiner

*Primary Examiner* — Igor N Borissov
(74) *Attorney, Agent, or Firm* — CALDWELL LLC

(57)          ABSTRACT

An apparatus and method for responding to a user query using a data structure are disclosed. The apparatus includes at least a processor and a memory communicatively connected to the at least a processor, wherein the memory contains instructions configuring the at least a processor to receive a plurality of sets of note data, wherein the plurality of sets of note data includes at least a temporal element, analyze the plurality of sets of note data using a machine-learning module, wherein the machine-learning module comprises a large language model, generate a cohort definition language data structure as a function of the analysis, receive a user query datum and generate a filtered datum as a function of the cohort definition language data structure and the user query datum.

18 Claims, 9 Drawing Sheets

APPARATUS AND METHOD FOR RESPONDING TO A USER QUERY BY GENERATING A DATA STRUCTURE

FIELD OF THE INVENTION

The present invention generally relates to the field of data analysis. In particular, the present invention is directed to apparatus and method for responding to a user query by generating a data structure.

BACKGROUND

In the field of data management and analytics, the ability to efficiently respond to user queries is of paramount importance. As data volumes grow exponentially, traditional methods of data retrieval and query response have become increasingly inadequate, often resulting in inefficiencies.

SUMMARY OF THE DISCLOSURE

In an aspect, an apparatus for responding to a user query using a data structure is disclosed. The apparatus includes at least a processor and a memory communicatively connected to the at least a processor, wherein the memory contains instructions configuring the at least a processor to receive a plurality of sets of note data, wherein the plurality of sets of note data includes at least a temporal element, analyze the plurality of sets of note data using a machine-learning module, wherein the machine-learning module comprises a large language model, generate a cohort definition language data structure as a function of the analysis, receive a user query datum and generate a filtered datum as a function of the cohort definition language data structure and the user query datum.

In another aspect, a method for responding to a user query using a data structure. The method includes receiving, using at least a processor, a plurality of sets of note data, wherein the plurality of sets of note data includes at least a temporal element, analyzing, using the at least a processor, the plurality of sets of note data using a machine-learning module, wherein the machine-learning module includes a large language model, generating, using the at least a processor, a cohort definition language data structure as a function of the analysis, receiving, using the at least a processor, a user query datum and generating, using the at least a processor, a filtered datum as a function of the cohort definition language data structure and the user query datum.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to apparatuses and methods for responding to a user query using a data structure are disclosed. The apparatus includes at least a processor and a memory communicatively connected to the at least a processor, wherein the memory contains instructions configuring the at least a processor to receive a plurality of sets of note data, wherein the plurality of sets of note data includes at least a temporal element, analyze the plurality of sets of note data using a machine-learning module, wherein the machine-learning module comprises a large language model, generate a cohort definition language data structure as a function of the analysis, receive a user query datum and generate a filtered datum as a function of the cohort definition language data structure and the user query datum. Exemplary embodiments illustrating aspects of the present disclosure are described below in the context of several specific examples.

Figure 1:
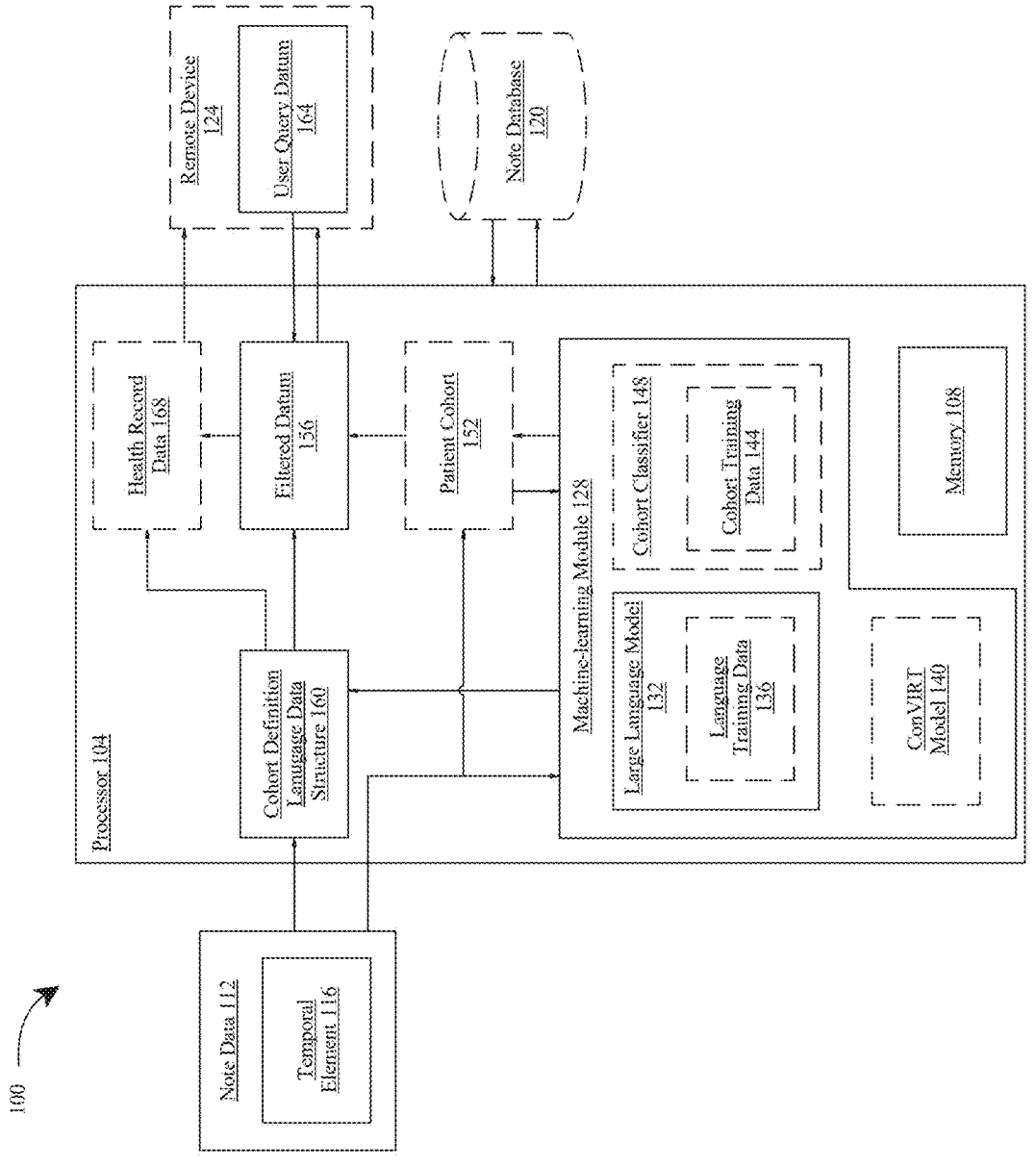
FIG. 1 illustrates a block diagram of an exemplary apparatus for responding to a user query by generating a data structure.

Referring now to FIG. 1, an exemplary embodiment of an apparatus 100 for responding to a user query using a data structure is illustrated. Apparatus 100 includes at least a processor 104. Processor 104 may include, without limitation, any processor described in this disclosure. Processor 104 may be included in a computing device. Processor 104 may include any computing device as described in this disclosure, including without limitation a microcontroller, microprocessor, digital signal processor (DSP) and/or system on a chip (SoC) as described in this disclosure. Processor 104 may include, be included in, and/or communicate with a mobile device such as a mobile telephone or smartphone. Processor 104 may include a single computing device operating independently, or may include two or more computing device operating in concert, in parallel, sequentially or the like; two or more computing devices may be included together in a single computing device or in two or more computing devices. Processor 104 may interface or communicate with one or more additional devices as described below in further detail via a network interface device. Network interface device may be utilized for connecting processor 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Processor 104 may include but is not limited to, for example, a computing device or cluster of computing devices in a first location and a second computing device or cluster of computing devices in a second location. Processor 104 may include one or more computing devices dedicated to data storage, security, distribution of traffic for load balancing, and the like. Processor 104 may distribute one or more computing tasks as described below across a plurality of computing devices of computing device, which may operate in parallel, in series, redundantly, or in any other manner used for distribution of tasks or memory between computing devices. Processor 104 may be implemented, as a non-limiting example, using a "shared nothing" architecture.

With continued reference to FIG. 1, processor 104 may be designed and/or configured to perform any method, method step, or sequence of method steps in any embodiment described in this disclosure, in any order and with any degree of repetition. For instance, processor 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Processor 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, apparatus 100 includes a memory 108 communicatively connected to processor 104. For the purposes of this disclosure, "communicatively connected" means connected by way of a connection, attachment or linkage between two or more relata which allows for reception and/or transmittance of information therebetween. For example, and without limitation, this connection may be wired or wireless, direct or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio and microwave data and/or signals, combinations thereof, and the like, among others. A communicative connection may be achieved, for example and without limitation, through wired or wireless electronic, digital or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

With continued reference to FIG. 1, memory 108 contains instructions configuring processor 104 to receive a plurality of sets of note data 112. For the purposes of this disclosure, "note data" is data related to documents regarding the health of one or more patients. As a non-limiting example, note data 112 may include electronic health record (EHR). For the purposes of this disclosure, an "electronic health record" is the systematized collection of patient and population electronically stored health information in a digital format. For example, and without limitation, note data 112 may include range of data related to health care, including patient demographics, patient identifier, medical history, medication and allergies, immunization status, laboratory test results, radiology images, vital signs, personal statistics like age and weight, billing information, and the like. For example, and without limitation, note data 112 may include medical information regarding patients subject to a clinical trial. In some embodiments, note data 112 may include clinicians' note related to a patient. In a non-limiting example, note data 112 may include clinicians' notes related to a disease that has been failed to be treated. In another non-limiting example, note data 112 may include text notes that are created by doctors that are related to patients, clinical trial documents, or the like. As another non-limiting example, note data 112 may include test results, dosage information, medication information, and the like. Test results may include any medical test modality, such as, but not limited to CT scans, MRIs, ECGs, EEGs, echocardiograms, and the like. As another non-limiting example, note data 112 may include a physical notes from clinicians related to patients. Note data 112 includes a temporal element 116. For the purposes of this disclosure, a "temporal element" is information related to date and/or time. As a non-limiting example, temporal element 116 may include the time and date of when the patient was diagnosed with disease, when the patient took medication or was given specific treatment, or the like. In some embodiments, note data 112 may be stored in a note database 120 as described further in detail below. In some embodiments, processor 104 may retrieve note data 112 from note database 120. In some embodiments, a user may manually input note data 112 into processor 104.

With continued reference to FIG. 1, processor 104 may receive note data 112 using an application programming interface (API). As used in the current disclosure, an "application programming interface" is a software interface for two or more computer programs to communicate with each other. As a non-limiting example, API may include EHR APIs, telemedicine APIs, and the like. An application programming interface may be a type of software interface, offering a service to other pieces of software. In contrast to a user interface, which connects a computer to a person, an application programming interface may connect computers or pieces of software to each other. An API may not be intended to be used directly by a person (e.g., the end user) other than a computer programmer who is incorporating it into the software. An API may be made up of different parts which act as tools or services that are available to the programmer. A program or a programmer that uses one of these parts is said to call that portion of the API. The calls that make up the API are also known as subroutines, methods, requests, or endpoints. An API specification may define these calls, meaning that it explains how to use or implement them. One purpose of API may be to hide the internal details of how a system works, exposing only those parts a programmer will find useful and keeping them consistent even if the internal details later change. An API may be custom-built for a particular pair of systems, or it may be a shared standard allowing interoperability among many systems. The term API may be often used to refer to web APIs, which allow communication between computers that are joined by the internet. API may be configured to query for web applications in order to retrieve note data 112 to another web application, database (e.g., note database 120), medical center patient portal, and the like. An API may be further configured to filter through web applications according to a filter criterion. In this disclosure, "filter criteria" are conditions the web applications must fulfill in order to qualify for API. Web applications may be filtered based on these filter criteria. Filter criteria may include, without limitation, types of medical facilities, location of the medical facility, and the like.

With continued reference to FIG. 1, in some embodiments, processor 104 may receive note data 112 from remote device 124. As a non-limiting example, remote device 124 may include a laptop, desktop, tablet, mobile phone, smart phone, smart watch, kiosk, smart headset, or things of the like. For the purposes of this disclosure, a "user" is any person, individual, organization or entity that is using or has used an apparatus. As a non-limiting example, user may include a physician, clinician, nurses, medical professionals, hospitals, medical organization, and the like. In some embodiments, remote device 124 may include an interface configured to receive inputs from user. In some embodiments, user may manually input any data into apparatus 100 using remote device 124. In some embodiments, user may have a capability to process, store or transmit any information independently.

With continued reference to FIG. 1, in some embodiments, apparatus 100 may include a note database 120. As used in this disclosure, "note database" is a data store configured to store data associated with note data. As a non-limiting example, note database 120 may store note data 112, information related to patients or users, and the like. In one or more embodiments, note database 120 may include inputted or calculated information and datum related to note data 112. In some embodiments, a datum history may be stored in note database 120. As a non-limiting example, the datum history may include real-time and/or previous inputted data related to note data 112. As a non-limiting example, note database 120 may include instructions from a user, who may be an expert user, a past user in embodiments disclosed herein, or the like, where the instructions may include examples of the data related to note data 112.

With continued reference to FIG. 1, in some embodiments, processor 104 may be communicatively connected with note database 120. For example, and without limitation, in some cases, note database 120 may be local to processor 104. In another example, and without limitation, note database 120 may be remote to processor 104 and communicative with processor 104 by way of one or more networks. The network may include, but is not limited to, a cloud network, a mesh network, and the like. By way of example, a "cloud-based" system can refer to a system which includes software and/or data which is stored, managed, and/or processed on a network of remote servers hosted in the "cloud," e.g., via the Internet, rather than on local severs or personal computers. A "mesh network" as used in this disclosure is a local network topology in which the infrastructure processor 104 connect directly, dynamically, and non-hierarchically to as many other computing devices as possible. A "network topology" as used in this disclosure is an arrangement of elements of a communication network. The network may use an immutable sequential listing to securely store note database 120. An "immutable sequential listing," as used in this disclosure, is a data structure that places data entries in a fixed sequential arrangement, such as a temporal sequence of entries and/or blocks thereof, where the sequential arrangement, once established, cannot be altered or reordered. An immutable sequential listing may be, include and/or implement an immutable ledger, where data entries that have been posted to the immutable sequential listing cannot be altered.

With continued reference to FIG. 1, in some embodiments, note database 120 may be implemented, without limitation, as a relational database, a key-value retrieval database such as a NOSQL database, or any other format or structure for use as a database that a person skilled in the art would recognize as suitable upon review of the entirety of this disclosure. Database may alternatively or additionally be implemented using a distributed data storage protocol and/or data structure, such as a distributed hash table or the like. Database may include a plurality of data entries and/or records as described in this disclosure. Data entries in a database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure.

With continued reference to FIG. 1, memory 108 contains instructions configuring processor 104 to analyze a plurality of sets of note data 112 using a machine-learning module 128. For the purposes of this disclosure, a "machine-learning module" is a machine-learning system that performs specific functions related to data processing, model training, inference, or evaluation using machine-learning models within the system. The machine-learning module 128 disclosed herein is further described in detail with respect to FIG. 5. Machine-learning module 128 includes a large language model 132. A "large language model," as used herein, is a deep learning data structure that can recognize, summarize, translate, predict and/or generate text and other content based on knowledge gained from massive datasets. Large language models 132 may be trained on large sets of data (e.g., language training data 136). Training sets may be drawn from diverse sets of data such as, as non-limiting examples, articles, research papers, unstructured data, electronic records, and the like. In some embodiments, training sets may include a variety of subject matters, such as, as nonlimiting examples, medical report documents, electronic health records, clinical research documents, and the like. In some embodiments, training sets of an LLM 132 may include information from one or more public or private databases. As a non-limiting example, training sets may include databases associated with a user or patient (e.g., note database 120). In some embodiments, training sets may include portions of documents associated with note data 112 correlated to examples of outputs (e.g., textual outputs). In an embodiment, an LLM 132 may include one or more architectures based on capability requirements of an LLM 132. Exemplary architectures may include, without limitation, GPT (Generative Pretrained Transformer), BERT (Bidirectional Encoder Representations from Transformers), T5 (Text-To-Text Transfer Transformer), and the like. Architecture choice may depend on a needed capability such generative, contextual, or other specific capabilities.

With continued reference to FIG. 1, in some embodiments, an LLM 132 may be generally trained. As used in this disclosure, a "generally trained" LLM is an LLM that is trained on a general training set comprising a variety of subject matters, data sets, and fields. In some embodiments, an LLM 132 may be initially generally trained. Additionally, or alternatively, an LLM 132 may be specifically trained. As used in this disclosure, a "specifically trained" LLM is an LLM that is trained on a specific training set, wherein the specific training set includes data including specific correlations for the LLM to learn. As a non-limiting example, an LLM 132 may be generally trained on a general training set, then specifically trained on a specific training set. In an embodiment, specific training of an LLM 132 may be performed using a supervised machine learning process. In some embodiments, generally training an LLM 132 may be performed using an unsupervised machine learning process. As a non-limiting example, specific training set may include information from a database. As a non-limiting example, specific training set may include text related to users or patients such as note data 112 correlated to examples of outputs. In an embodiment, training one or more machine learning models may include setting the parameters of the one or more models (weights and biases) either randomly or using a pretrained model. Generally training one or more machine learning models on a large corpus of text data can provide a starting point for fine-tuning on a specific task. A model such as an LLM 132 may learn by adjusting its parameters during the training process to minimize a defined loss function, which measures the difference between predicted outputs and ground truth. Once a model has been generally trained, the model may then be specifically trained to fine-tune the pretrained model on task-specific data to adapt it to the target task. Fine-tuning may involve training a model with task-specific training data, adjusting the model's weights to optimize performance for the particular task. In some cases, this may include optimizing the model's performance by fine-tuning hyperparameters such as learning rate, batch size, and regularization. Hyperparameter tuning may help in achieving the best performance and convergence during training. In an embodiment, fine-tuning a pretrained model such as an LLM 132 may include fine-tuning the pretrained model using Low-Rank Adaptation (LoRA). As used in this disclosure, "Low-Rank Adaptation" is a training technique for large language models that modifies a subset of parameters in the model. Low-Rank Adaptation may be configured to make the training process more computationally efficient by avoiding a need to train an entire model from scratch. In an exemplary embodiment, a subset of parameters that are updated may include parameters that are associated with a specific task or domain. In some embodiments, LLM 132 may be iteratively trained as a function of previous iterations. In some embodiments, processor 104 may update training set (e.g., language training data 136) as a function of note data 112, output of LLM 132, or the like and retrain LLM 132 using updated training set.

With continued reference to FIG. 1, in some embodiments an LLM 132 may include and/or be produced using Generative Pretrained Transformer (GPT), GPT-2, GPT-3, GPT-4, and the like. GPT, GPT-2, GPT-3, GPT-3.5, and GPT-4 are products of Open AI Inc., of San Francisco, CA. An LLM 132 may include a text prediction based algorithm configured to receive an article and apply a probability distribution to the words already typed in a sentence to work out the most likely word to come next in augmented articles. For example, if some words that have already been typed are "The change in blood," then it may be highly likely that the word "pressure" will come next. An LLM 132 may output such predictions by ranking words by likelihood or a prompt parameter. For the example given above, an LLM 132 may score "pressure" as the most likely, "flow" as the next most likely, "oxygen levels" or "viscosity" next, and the like. An LLM 132 may include an encoder component and a decoder component.

Still referring to FIG. 1, an LLM 132 may include a transformer architecture. In some embodiments, encoder component of an LLM 132 may include transformer architecture. A "transformer architecture," for the purposes of this disclosure is a neural network architecture that uses self-attention and positional encoding. Transformer architecture may be designed to process sequential input data, such as natural language, with applications towards tasks such as translation and text summarization. Transformer architecture may process the entire input all at once. "Positional encoding," for the purposes of this disclosure, refers to a data processing technique that encodes the location or position of an entity in a sequence. In some embodiments, each position in the sequence may be assigned a unique representation. In some embodiments, positional encoding may include mapping each position in the sequence to a position vector. In some embodiments, trigonometric functions, such as sine and cosine, may be used to determine the values in the position vector. In some embodiments, position vectors for a plurality of positions in a sequence may be assembled into a position matrix, wherein each row of position matrix may represent a position in the sequence.

With continued reference to FIG. 1, an LLM 132 and/or transformer architecture may include an attention mechanism. An "attention mechanism," as used herein, is a part of a neural architecture that enables a system to dynamically quantify the relevant features of the input data. In the case of natural language processing, input data may be a sequence of textual elements. It may be applied directly to the raw input or to its higher-level representation.

With continued reference to FIG. 1, attention mechanism may represent an improvement over a limitation of an encoder-decoder model. An encoder-decider model encodes an input sequence to one fixed length vector from which the output is decoded at each time step. This issue may be seen as a problem when decoding long sequences because it may make it difficult for the neural network to cope with long sentences, such as those that are longer than the sentences in the training corpus. Applying an attention mechanism, an LLM 132 may predict the next word by searching for a set of positions in a source sentence where the most relevant information is concentrated. An LLM 132 may then predict the next word based on context vectors associated with these source positions and all the previously generated target words, such as textual data of a dictionary correlated to a prompt in a training data set. A "context vector," as used herein, are fixed-length vector representations useful for document retrieval and word sense disambiguation.

Still referring to FIG. 1, attention mechanism may include, without limitation, generalized attention self-attention, multi-head attention, additive attention, global attention, and the like. In generalized attention, when a sequence of words or an image is fed to an LLM 132, it may verify each element of the input sequence and compare it against the output sequence. Each iteration may involve the mechanism's encoder capturing the input sequence and comparing it with each element of the decoder's sequence. From the comparison scores, the mechanism may then select the words or parts of the image that it needs to pay attention to. In self-attention, an LLM 132 may pick up particular parts at different positions in the input sequence and over time compute an initial composition of the output sequence. In multi-head attention, an LLM 132 may include a transformer model of an attention mechanism. Attention mechanisms, as described above, may provide context for any position in the input sequence. For example, if the input data is a natural language sentence, the transformer does not have to process one word at a time. In multi-head attention, computations by an LLM 132 may be repeated over several iterations, each computation may form parallel layers known as attention heads. Each separate head may independently pass the input sequence and corresponding output sequence element through a separate head. A final attention score may be produced by combining attention scores at each head so that every nuance of the input sequence is taken into consideration. In additive attention (Bahdanau attention mechanism), an LLM 132 may make use of attention alignment scores based on a number of factors. Alignment scores may be calculated at different points in a neural network, and/or at different stages represented by discrete neural networks. Source or input sequence words are correlated with target or output sequence words but not to an exact degree. This correlation may take into account all hidden states and the final alignment score is the summation of the matrix of alignment scores. In global attention (Luong mechanism), in situations where neural machine translations are required, an LLM 132 may either attend to all source words or predict the target sentence, thereby attending to a smaller subset of words.

With continued reference to FIG. 1, multi-headed attention in encoder may apply a specific attention mechanism called self-attention. Self-attention allows models such as an LLM 132 or components thereof to associate each word in the input, to other words. As a non-limiting example, an LLM 132 may learn to associate the word "you", with "how" and "are". It's also possible that an LLM 132 learns that words structured in this pattern are typically a question and to respond appropriately. In some embodiments, to achieve self-attention, input may be fed into three distinct fully connected neural network layers to create query, key, and value vectors. A query vector may include an entity's learned representation for comparison to determine attention score. A key vector may include an entity's learned representation for determining the entity's relevance and attention weight. A value vector may include data used to generate output representations. Query, key, and value vectors may be fed through a linear layer; then, the query and key vectors may be multiplied using dot product matrix multiplication in order to produce a score matrix. The score matrix may determine the amount of focus for a word should be put on other words (thus, each word may be a score that corresponds to other words in the time-step). The values in score matrix may be scaled down. As a non-limiting example, score matrix may be divided by the square root of the dimension of the query and key vectors. In some embodiments, the softmax of the scaled scores in score matrix may be taken. The output of this softmax function may be called the attention weights. Attention weights may be multiplied by your value vector to obtain an output vector. The output vector may then be fed through a final linear layer.

Still referencing FIG. 1, in order to use self-attention in a multi-headed attention computation, query, key, and value may be split into N vectors before applying self-attention. Each self-attention process may be called a "head." Each head may produce an output vector and each output vector from each head may be concatenated into a single vector. This single vector may then be fed through the final linear layer discussed above. In theory, each head can learn something different from the input, therefore giving the encoder model more representation power.

With continued reference to FIG. 1, encoder of transformer may include a residual connection. Residual connection may include adding the output from multi-headed attention to the positional input embedding. In some embodiments, the output from residual connection may go through a layer normalization. In some embodiments, the normalized residual output may be projected through a pointwise feed-forward network for further processing. The pointwise feed-forward network may include a couple of linear layers with a ReLU activation in between. The output may then be added to the input of the pointwise feed-forward network and further normalized.

Continuing to refer to FIG. 1, transformer architecture may include a decoder. Decoder may a multi-headed attention layer, a pointwise feed-forward layer, one or more residual connections, and layer normalization (particularly after each sub-layer), as discussed in more detail above. In some embodiments, decoder may include two multi-headed attention layers. In some embodiments, decoder may be autoregressive. For the purposes of this disclosure, "autoregressive" means that the decoder takes in a list of previous outputs as inputs along with encoder outputs containing attention information from the input.

With further reference to FIG. 1, in some embodiments, input to decoder may go through an embedding layer and positional encoding layer in order to obtain positional embeddings. Decoder may include a first multi-headed attention layer, wherein the first multi-headed attention layer may receive positional embeddings.

With continued reference to FIG. 1, first multi-headed attention layer may be configured to not condition to future tokens. As a non-limiting example, when computing attention scores on the word "am," decoder should not have access to the word "fine" in "I am fine," because that word is a future word that was generated after. The word "am" should only have access to itself and the words before it. In some embodiments, this may be accomplished by implementing a look-ahead mask. Look ahead mask is a matrix of the same dimensions as the scaled attention score matrix that is filled with "0s" and negative infinities. For example, the top right triangle portion of look-ahead mask may be filled with negative infinities. Look-ahead mask may be added to scaled attention score matrix to obtain a masked score matrix. Masked score matrix may include scaled attention scores in the lower-left triangle of the matrix and negative infinities in the upper-right triangle of the matrix. Then, when the softmax of this matrix is taken, the negative infinities will be zeroed out; this leaves zero attention scores for "future tokens".

Still referring to FIG. 1, second multi-headed attention layer may use encoder outputs as queries and keys and the outputs from the first multi-headed attention layer as values. This process matches the encoder's input to the decoder's input, allowing the decoder to decide which encoder input is relevant to put a focus on. The output from second multi-headed attention layer may be fed through a pointwise feedforward layer for further processing.

With continued reference to FIG. 1, the output of the pointwise feedforward layer may be fed through a final linear layer. This final linear layer may act as a classifier. This classifier may be as big as the number of classes that you have. For example, if you have 10,000 classes for 10,000 words, the output of that classifier will be of size 10,000. The output of this classifier may be fed into a softmax layer which may serve to produce probability scores between zero and one. The index may be taken of the highest probability score in order to determine a predicted word.

Still referring to FIG. 1, decoder may take this output and add it to the decoder inputs. Decoder may continue decoding until a token is predicted. Decoder may stop decoding once it predicts an end token.

Continuing to refer to FIG. 1, in some embodiment, decoder may be stacked N layers high, with each layer taking in inputs from the encoder and layers before it. Stacking layers may allow an LLM 132 to learn to extract and focus on different combinations of attention from its attention heads.

With continued reference to FIG. 1, an LLM 132 may receive an input. Input may include a string of one or more characters. Inputs may additionally include unstructured data. For example, input may include one or more words, a sentence, a paragraph, a thought, a query, and the like. A "query" for the purposes of the disclosure is a string of characters that poses a question. In some embodiments, input may be received from a user device. User device may be any computing device that is used by a user. As non-limiting examples, user device may include desktops, laptops, smartphones, tablets, and the like. In some embodiments, input may include any set of data associated with note data 112.

With continued reference to FIG. 1, an LLM 132 may generate at least one annotation as an output. At least one annotation may be any annotation as described herein. In some embodiments, an LLM 132 may include multiple sets of transformer architecture as described above. Output may include a textual output. A "textual output," for the purposes of this disclosure is an output comprising a string of one or more characters. Textual output may include, for example, a plurality of annotations for unstructured data. In some embodiments, textual output may include a phrase or sentence summarizing or representing note data 112 (e.g., keywords). In some embodiments, textual output may include a sentence or plurality of sentences describing temporal element 116 of note data 112. As a non-limiting example, textual output may include timing, medications, treatments, patient demographics, medical histories, and the like.

With continued reference to FIG. 1, in some embodiments, processor 104 may be configured to analyze note data 112 using machine vision system. For the purposes of this disclosure, a "machine vision system" is a type of technology that enables a computing device to inspect, evaluate and identify still or moving images. In a non-limiting example, processor 104 may analyze ECG, X-ray, and the like of note data 112 using machine vision system and generate textual outputs as a function of the analysis by implementing an image classifier trained with image training data; the image classifier may be configured to classify the output of machine vision system into label (e.g., textual output) of note data 112. Alternatively, this may be performed without using computer vision and/or classification; for instance, a user may input an identification of textual outputs in note data 112. In some cases, a machine vision system may be used for world modeling or registration of objects within a space. In some cases, registration may include image processing, such as without limitation object recognition, feature detection, edge/corner detection, and the like. Non-limiting example of feature detection may include scale invariant feature transform (SIFT), Canny edge detection, Shi Tomasi corner detection, and the like. In some cases, a machine vision process may operate image classification and segmentation models, such as without limitation by way of machine vision resource (e.g., OpenMV or TensorFlow Lite). A machine vision process may detect motion, for example by way of frame differencing algorithms. A machine vision process may detect markers, for example blob detection, object detection, face detection, and the like. In some cases, a machine vision process may perform eye tracking (i.e., gaze estimation). In some cases, a machine vision process may perform person detection, for example by way of a trained machine learning model. In some cases, a machine vision process may perform motion detection (e.g., camera motion and/or object motion), for example by way of optical flow detection. In some cases, machine vision process may perform code (e.g., barcode) detection and decoding. In some cases, a machine vision process may additionally perform image capture and/or video recording.

With continued reference to FIG. 1, in some cases, registration may include one or more transformations to orient a camera frame (or an image or video stream) relative a three-dimensional coordinate system; exemplary transformations include without limitation homography transforms and affine transforms. In an embodiment, registration of first frame to a coordinate system may be verified and/or corrected using object identification and/or computer vision, as described above. For instance, and without limitation, an initial registration to two dimensions, represented for instance as registration to the x and y coordinates, may be performed using a two-dimensional projection of points in three dimensions onto a first frame, however. A third dimension of registration, representing depth and/or a z axis, may be detected by comparison of two frames; for instance, where first frame includes a pair of frames captured using a pair of cameras (e.g., stereoscopic camera also referred to in this disclosure as stereo-camera), image recognition and/or edge detection software may be used to detect a pair of stereoscopic views of images of an object; two stereoscopic views may be compared to derive z-axis values of points on object permitting, for instance, derivation of further z-axis points within and/or around the object using interpolation. This may be repeated with multiple objects in field of view, including without limitation environmental features of interest identified by object classifier and/or indicated by an operator. In an embodiment, x and y axes may be chosen to span a plane common to two cameras used for stereoscopic image capturing and/or an xy plane of a first frame; a result, x and y translational components and φ may be pre-populated in translational and rotational matrices, for affine transformation of coordinates of object, also as described above. Initial x and y coordinates and/or guesses at transformational matrices may alternatively or additionally be performed between first frame and second frame, as described above. For each point of a plurality of points on object and/or edge and/or edges of object as described above, x and y coordinates of a first stereoscopic frame may be populated, with an initial estimate of z coordinates based, for instance, on assumptions about object, such as an assumption that ground is substantially parallel to an xy plane as selected above. Z coordinates, and/or x, y, and z coordinates, registered using image capturing and/or object identification processes as described above may then be compared to coordinates predicted using initial guess at transformation matrices; an error function may be computed using by comparing the two sets of points, and new x, y, and/or z coordinates, may be iteratively estimated and compared until the error function drops below a threshold level.

With continued reference to FIG. 1, in some embodiments, processor 104 may analyze note data 112 using a Contrastive Visual Representation Learning from Text (ConVIRT model) model 140 or ConVIRT model 140. For the purposes of this disclosure, a "Contrastive Visual Representation Learning from Text model" is a machine learning framework designed to enhance visual representation learning by leveraging textual information through a contrastive learning approach. For the purposes of this disclosure, a "contrastive learning" is a self-supervised learning approach that aims to learn effective representations by distinguishing between similar (positive) and dissimilar (negative) pairs of data points. In some embodiments, machine-learning module 128 may include ConVIRT model 140 model configured to learn visual representations by exploiting naturally occurring pairing of images and textual data. ConVIRT model 140 model may be configured to extract meaningful representations from unlabeled data by mapping similar instances close together in a latent space while pushing apart dissimilar instances. As a non-limiting example, ConVIRT model 140 may be configured to learn visual representations by exploiting pairing of note data 112 and textual outputs. In some embodiments, ConVIRT model 140 may generate image-text pairs, which may be received as input to LLM 132. Additional details of ConVIRT model 140 is described with respect to FIG. 4. A person of ordinary skill in the art, upon reviewing the entirety of this disclosure, will be able to recognize suitable means to implement ConVIRT model 140 and its related aspects for apparatus 100.

With continued reference to FIG. 1, in some embodiments, processor 104 may be configured to generate cohort training data 144. In a non-limiting example, cohort training data 144 may include correlations between exemplary note data and exemplary patient cohorts. In some embodiments, cohort training data 144 may be stored in note database 120. In some embodiments, cohort training data 144 may be received from one or more users, note database 120, external computing devices, and/or previous iterations of processing. As a non-limiting example, cohort training data 144 may include instructions from a user, who may be an expert user, a past user in embodiments disclosed herein, or the like, which may be stored in memory and/or stored in note database 120, where the instructions may include labeling of training examples. In some embodiments, cohort training data 144 may be updated iteratively using a feedback loop. As a non-limiting example, processor 104 may update cohort training data 144 iteratively through a feedback loop as a function of note data 112, patient data, patient cohorts, or the like. In some embodiments, processor 104 may be configured to generate cohort classifier 148. In some embodiments, machine-learning module 128 may include cohort classifier 148. In a non-limiting example, generating cohort classifier 148 may include training, retraining, or fine-tuning cohort classifier 148 using cohort training data 144 or updated cohort training data 144. In some embodiments, processor 104 may be configured to classify patient cohorts 152 using cohort classifier 148 (i.e. trained or updated cohort classifier 148). In some embodiments, a patient may be classified to a patient cohort 152 and processor 104 may generate filtered datum 156 based on the patient cohort using cohort definition language data structure 160 and the resulting output may be used to update cohort training data 144. In some embodiments, generating training data and training machine-learning models may be simultaneous. For the purposes of this disclosure, a "patient cohort" is a specific group of patients identified and selected based on shared characteristics or conditions. As a non-limiting example, characteristics of patient cohort 152 may include demographic of a patient; for instance, age, gender, ethnicity, and the like. As another non-limiting example, characteristics of patient cohort 152 may include medical history or medical condition; for instance, diagnoses, comorbidities, treatment histories, medication histories, weights, existing conditions, and the like. In some embodiments, user may manually input patient cohorts 152. In some embodiments, processor 104 may retrieve patient cohorts 152 from note database 120.

With continued reference to FIG. 1, memory 108 contains instructions configuring processor 104 to generate a cohort definition language data structure 160 as a function of analysis of note data 112. For the purposes of this disclosure, a "cohort definition language data structure" refers to the relationship or connection established between two or more elements of data used to define and describe groups of patients, known as cohorts, based on specific criteria. As a non-limiting example, the specific criteria may include age, ethnicity, existing health condition or disease, weight, gender, temporal features, and the like. For example, and without limitation, cohort definition language data structure 160 may include a plurality of temporal criteria related to a time of treatment. For the purposes of this disclosure, "temporal criteria" is time-related aspects and conditions that define the inclusion and exclusion parameters. As a non-limiting example, temporal criteria may include temporal element 116 related to time period for diagnoses or conditions, time of treatment, age at event, medication intake, and the like. As another non-limiting example, the specific criteria may include an inclusion and exclusion criteria. In a non-limiting example, cohort definition language data structure 160 may include a formal, standardized framework used to specify the attributes, inclusion and exclusion criteria, and logical conditions necessary to define a group of patients (e.g., a cohort) for analytical or clinical purposes. For the purposes of this disclosure, an "inclusion and exclusion criteria" is a criteria that defines the characteristics that prospective participants or patients must possess (inclusion criteria) or lack (exclusion criteria) in order to be eligible for enrollment in a study. For example, and without limitation, cohort definition language data structure 160 may include a standardized framework used to specify criteria for specific clinical trial. For example, and without limitation, cohort definition language data structure 160 may include a standardized framework of medications and treatments for a cohort of patients. As a non-limiting example, cohort definition language data structure 160 may include a decision tree, tree diagram, or the like. As another non-limiting example, cohort definition language data structure 160 may include a JavaScript Object Notation (JSON) format. For example, and without limitation, cohort definition language data structure 160 may include {"id": "med123", "name": "John Doc", "dose": "10 mg", "route": "oral", "frequency": "once daily", "startDate": "2023 Jan. 1", "endDate": "2023 Dec. 31", "prescribingDoctor": {"id": "doc456", "name": "Dr. Smith"}}. Cohort definition language data structure 160 may be a representation of a plurality of data associated with note data 112 and/or textual outputs. Cohort definition language data structure 160 may include a parametric map that takes high dimensional raw data and abstracts it into a lower dimensional feature vector that ideally encapsulates the essential information. Cohort definition language data structure 160 may involve linking or integrating note data 112 and/or textual outputs with the descriptive or explanatory multi-modal data to provide additional context, enhance understanding, and convey relevant information. In an embodiment, cohort definition language data structure 160 may include a relationship or connection between note data 112 and/or textual outputs. In another embodiment, cohort definition language data structure 160 may include a relationship or connection between note data 112 and/or textual outputs. Cohort definition language data structure 160 may include a longitudinal record of a patient's health history. By linking note data 112 and/or textual outputs to each other, processor 104 can track and analyze the cardiac relationships of note data 112 and/or textual outputs. This longitudinal perspective enables the identification of trends, changes, or patterns in note data 112 and/or textual outputs.

With continued reference to FIG. 1, in some embodiments, processor 104 may generate a plurality of cohort definition language data structures 160 and each of the plurality of cohort definition language data structures 160 may include different analytical, clinical purpose or inclusion and exclusion criteria including a plurality of temporal criteria. In some embodiments, one cohort definition language data structure 160 may include a plurality of different inclusion and exclusion criteria including a plurality of temporal criteria. As a non-limiting example, first cohort definition language data structure may be related to a first clinical trial and second cohort definition language data structure may be related to a second clinical trial. As another non-limiting example, first cohort definition language data structure may be related to a first patient and second cohort definition language data structure may be related to a second patient. As another non-limiting example, one cohort definition language data structure 160 may include first criteria related to patients with diagnoses A that took medication B within a specific time period and second criteria related to patients with diagnoses B that took medication A within a specific time period. in some embodiments, processor 104 may determine one cohort definition language data structure 160 related to user query datum 164 from a plurality of cohort language data structures 160 or determine one inclusion and exclusion criteria related to user query datum 164 from one cohort definition language data structure 160 by using keywords of user query datum 164. In some embodiments, processor 104 may generate cohort definition language data structure 160 as a function of temporal element 116 of note data 112. As a non-limiting example, each layer of decision tree of the cohort definition language data structure 160 may represent different sequential dates. For instance, the first layer could correspond to the most recent timeline, while subsequent layers could reflect progressively later timelines. In a non-limiting example, the first layer could correspond to the most recently administered medication or medical treatment, with subsequent layers reflecting progressively earlier instances. In some embodiments, each node of decision tree of cohort definition language data structure 160 may include temporal element 116.

With continued reference to FIG. 1, in some embodiments, processor 104 may be configured to query a note database 120 or API for health record data 168 as a function of filtered datum 156. For the purposes of this disclosure, "health record data" is information collected, stored, or managed within electronic health records systems. As a non-limiting example, health record data 168 may include a patient's health status, medical history, healthcare information, and the like. In some embodiments, processor 104 may query note database 120 or EHR API to retrieve health record data 168 as a function of a set of filtered temporal criteria. In some embodiments, filtered temporal criteria may be consistent with temporal criteria; filtered temporal criteria of filtered datum 156 may be a temporal criteria of cohort definition language data structure 160 that is related to user query datum 164.

With continued reference to FIG. 1, cohort definition language data structure 160 may be represented in vector form. A vector representing cohort definition language data structure 160 is a mathematical construct that can be used to represent multiple data points or variables. In the context of healthcare or any other domain, a vector can be constructed to capture and represent a diverse set of data points. A vector has a certain number of dimensions, which may correspond to the number of data points or variables being represented. Each dimension in the vector corresponds to a specific data point or variable. Each dimension in the vector represents a distinct data point or variable. For example, in the healthcare domain, these data points could include patient demographics (e.g., age, gender), medical history (e.g., conditions, medications, surgeries), laboratory results (e.g., cholesterol levels, glucose levels), vital signs (e.g., blood pressure, heart rate), clinical trial histories, or any other relevant healthcare-related information. Values within each dimension of the vector, there are corresponding values that represent the specific data point or variable. These values can be numerical, categorical, or symbolic, depending on the nature of the data being represented. In an embodiment, cohort definition language data structure 160 represented as a vector may be used to convey a large amount of information regarding the patient. This may include information regarding note data 112 and/or textual outputs, and the like. In a non-limiting example, a cohort definition language data structure 160 in vector form may represent all or part of medications, surgeries, treatments, and the like that a patient has had. Additionally, a cohort definition language data structure 160 in vector form may represent all or part of patient demographics, medical history, past and present diagnosis, past and present medical procedures, medications, laboratory results, clinical notes.

With continued reference to FIG. 1, processor 104 may generate cohort definition language data structure 160 using a structure machine-learning model. As used in the current disclosure, a "structure machine machine-learning model" is a machine-learning model that is configured to generate cohort definition language data structure. The structure machine machine-learning model may be consistent with the machine-learning model or classifier described below in FIG. 5. Inputs to the structure machine-learning model may include note data 112, textual outputs, and the like. Outputs to the structure machine-learning model may include cohort definition language data structure 160. The structure machine-learning model may be configured to generate representations of data from several different modalities. Structure training data may include a plurality of data entries containing a plurality of inputs that are correlated to a plurality of outputs for training a processor by a machine-learning process. In an embodiment, structure training data may include note data examples and/or textual output examples correlated to examples of cohort definition data structure. Structure training data may be received from note database 120. In an embodiment, structure training data may be iteratively updated as a function of the input and output results of past structure machine-learning model or any other machine-learning model mentioned throughout this disclosure. The machine-learning model may be performed using, without limitation, linear machine-learning models such as without limitation logistic regression and/or naive Bayes machine-learning models, nearest neighbor machine-learning models such as k-nearest neighbors machine-learning models, support vector machines, least squares support vector machines, fisher's linear discriminant, quadratic machine-learning models, decision trees, boosted trees, random forest machine-learning model, and the like.

With continued reference to FIG. 1, memory 108 contains instructions configuring processor 104 to receive a user query datum 164. For the purposes of this disclosure, a "user query datum" is a data element including a query that is made by a user. As a non-limiting example, user query datum 164 may include a query related to patient's demographic, medical history, and the like. For example, and without limitation, user query datum 164 may include 'when did this patient begin taking the drug?' As another non-limiting example, user query datum 164 may include a query related to eligibility to a program. For example, and without limitation, user query datum 164 may include 'is this patient eligible to a clinical trial?' In some embodiments, processor 104 may receive user query datum 164 from a chatbot. For the purposes of this disclosure, "chatbot" is an artificial intelligence (AI) program designed to simulate human conversation or interaction through text, voice-based or image-based communication. The chatbot disclosed herein is further described with respect to FIG. 3. In some embodiments, user query datum 164 may be stored in note database 120 and processor 104 may retrieve user query datum 164 from note database 120. In some embodiments, user may manually input user query datum 164.

With continued reference to FIG. 1, in some embodiments, user query datum 164 may include patient data. For the purposes of this disclosure, "patient data" is data related to a patient that a user wants to inquire about. As a non-limiting example, user query datum 164 may include any information related to a patient that a user is interested in. For example, and without limitation, patient data may include patient demographic, medical history (e.g., medication, treatment, surgery, and the like), and the like of a patient that a doctor (e.g., user) wants to know if the patient is eligible for a specific clinical trial. For example, and without limitation, patient data may include patient demographic of a patient that a doctor (e.g., user) wants to know medical history of a patient. In some embodiments, user may manually input patient data. In some embodiments, patient data may be stored in note database 120 and processor 104 may retrieve patient data from note database 120. In some embodiments, user may input patient data using a chatbot.

With continued reference to FIG. 1, in some embodiments, processor 104 may use a language processing module to analyze user query datum 164 and/or patient data. The language processing module may be configured to extract, from user query datum 164, note data 112 or patient data, one or more words. One or more words may include, without limitation, strings of one or more characters, including without limitation any sequence or sequences of letters, numbers, punctuation, diacritic marks, engineering symbols, medical symbols and abbreviations and formulas, spaces, whitespace, and other symbols, including any symbols usable as textual data as described above. Textual data may be parsed into tokens, which may include a simple word (sequence of letters separated by whitespace) or more generally a sequence of characters as described previously. The term "token," as used herein, refers to any smaller, individual groupings of text from a larger source of text; tokens may be broken up by word, pair of words, sentence, or other delimitation. These tokens may in turn be parsed in various ways. Textual data may be parsed into words or sequences of words, which may be considered words as well. Textual data may be parsed into "n-grams", where all sequences of n consecutive characters are considered. Any or all possible sequences of tokens or words may be stored as "chains", for example for use as a Markov chain or Hidden Markov Model.

With continued reference to FIG. 1, language processing module may operate to produce a language processing model. Language processing model may include a program automatically generated by processor 104 and/or language processing module to produce associations between one or more words extracted from at least a document and detect associations, including without limitation mathematical associations, between such words. Associations between language elements, where language elements include for purposes herein extracted words, relationships of such categories to other such term may include, without limitation, mathematical associations, including without limitation statistical correlations between any language element and any other language element and/or language elements. Statistical correlations and/or mathematical associations may include probabilistic formulas or relationships indicating, for instance, a likelihood that a given extracted word indicates a given category of semantic meaning. As a further example, statistical correlations and/or mathematical associations may include probabilistic formulas or relationships indicating a positive and/or negative association between at least an extracted word and/or a given semantic meaning; positive or negative indication may include an indication that a given document is or is not indicating a category semantic meaning. Whether a phrase, sentence, word, or other textual element in a document or corpus of documents constitutes a positive or negative indicator may be determined, in an embodiment, by mathematical associations between detected words, comparisons to phrases and/or words indicating positive and/or negative indicators that are stored in memory at computing device, or the like.

With continued reference to FIG. 1, language processing module may generate the language processing model by any suitable method, including without limitation a natural language processing classification algorithm; language processing model may include a natural language process classification model that enumerates and/or derives statistical relationships between input terms and output terms. Algorithm to generate language processing model may include a stochastic gradient descent algorithm, which may include a method that iteratively optimizes an objective function, such as an objective function representing a statistical estimation of relationships between terms, including relationships between input terms and output terms, in the form of a sum of relationships to be estimated. In an alternative or additional approach, sequential tokens may be modeled as chains, serving as the observations in a Hidden Markov Model (HMM). HMMs, as used herein, are statistical models with inference algorithms that that may be applied to the models. In such models, a hidden state to be estimated may include an association between an extracted words, phrases, and/or other semantic units. There may be a finite number of categories to which an extracted word may pertain; an HMM inference algorithm, such as the forward-backward algorithm or the Viterbi algorithm, may be used to estimate the most likely discrete state given a word or sequence of words. Language processing module may combine two or more approaches. For instance, and without limitation, machine-learning program may use a combination of Naive-Bayes (NB), Stochastic Gradient Descent (SGD), and parameter grid-searching classification techniques; the result may include a classification algorithm that returns ranked associations.

With continued reference to FIG. 1, generating language processing model may include generating a vector space, which may be a collection of vectors, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each vector in an n-dimensional vector space may be represented by an n-tuple of numerical values. Each unique extracted word and/or language element as described above may be represented by a vector of the vector space. In an embodiment, each unique extracted and/or other language element may be represented by a dimension of vector space; as a non-limiting example, each element of a vector may include a number representing an enumeration of co-occurrences of the word and/or language element represented by the vector with another word and/or language element. Vectors may be normalized, scaled according to relative frequencies of appearance and/or file sizes. In an embodiment associating language elements to one another as described above may include computing a degree of vector similarity between a vector representing each language element and a vector representing another language element; vector similarity may be measured according to any norm for proximity and/or similarity of two vectors, including without limitation cosine similarity, which measures the similarity of two vectors by evaluating the cosine of the angle between the vectors, which can be computed using a dot product of the two vectors divided by the lengths of the two vectors. Degree of similarity may include any other geometric measure of distance between vectors.

With continued reference to FIG. 1, language processing module may use a corpus of documents to generate associations between language elements in a language processing module may then use such associations to analyze words extracted from one or more documents and determine that the one or more documents indicate significance of a category. In an embodiment, language module and/or processor 104 may perform this analysis using a selected set of significant documents, such as documents identified by one or more experts as representing good information; experts may identify or enter such documents via graphical user interface or may communicate identities of significant documents according to any other suitable method of electronic communication, or by providing such identity to other persons who may enter such identifications into processor 104. Documents may be entered into a computing device by being uploaded by an expert or other persons using, without limitation, file transfer protocol (FTP) or other suitable methods for transmission and/or upload of documents; alternatively or additionally, where a document is identified by a citation, a uniform resource identifier (URI), uniform resource locator (URL) or other datum permitting unambiguous identification of the document, processor 104 may automatically obtain the document using such an identifier, for instance by submitting a request to a database or compendium of documents such as JSTOR as provided by Ithaka Harbors, Inc. of New York.

With continued reference to FIG. 1, memory 108 contains instructions configuring processor 104 to generate a filtered datum 156 as a function of user query datum 164 and cohort definition language data structure 160. For the purposes of this disclosure, a "filtered datum" is an element of data that contains a response to a user's query, wherein the datum is generated using a cohort definition language data structure. In some embodiments, filtered datum 156 may be related to an inclusion and exclusion criteria for a specific group of patients from cohort definition language data structure 160. For example, and without limitation, filtered datum 156 may include a filtered temporal criteria. For the purposes of this disclosure, a "filtered temporal criteria" is time-related aspects and conditions that define the inclusion and exclusion parameters for a specific patient or group of patients whom a user is querying about. As a non-limiting example, filtered temporal criteria may include a temporal element 116 related to a time of treatment, time period of diagnoses, medication intakes, and the like related to user query datum 164. As a non-limiting example, when user query datum 164 includes 'when did this patient begin taking the drug?,' processor 104 may generate filtered datum 156 as '12 months.' In some embodiments, user query datum 164 may include "what are the outcomes for patients that have X condition and have been taking Y drug for three months? In some embodiments, filtered datum 156 may include patient data relating to patients that have X condition and have been taking Y drug for three months. In some embodiments, filtered datum 156 may inclusion/exclusion criteria defining a cohort of patients that have X condition and have been taking Y drug for three months. As another non-limiting example, when user query datum 164 includes 'is this patient eligible for this clinical trial?,' processor 104 may generate filtered datum 156 as 'no.' In some embodiments, processor 104 may generate a subsequent filtered datum. For the purposes of this disclosure, a "subsequent filtered datum" is an element of data that contains a response to a user's query that provides context or explanation for generated filtered datum. In some embodiments, subsequent filtered datum may include an explanation, description, or the like that can deliver a reasoning of generated filtered datum 156 as a function of user query datum 164 using a cohort definition language data structure 160. For example, and without limitation, when user query datum 164 includes 'when did this patient begin taking the drug?' and filtered datum 156 includes '12 months,' processor 104 may generate a subsequent filtered datum that includes 'the patient has taken the drug from Jun. 24, 2023, to Jun. 25, 2024.' As another non-limiting example, when user query datum 164 includes 'is this patient eligible for this clinical trial?' and filtered datum 156 includes 'no,' processor 104 may generate a subsequent filtered datum that includes 'the patient took a specific medication that is not acceptable to be eligible for the clinical trial' or 'the patient took a specific medication within a specific time period.' In some embodiments, generating a filtered datum 156 may include transiting user query datum 164 through a decision tree, JSON format, and the like (e.g., cohort definition language data structure 160). In some embodiments, processor 104 may generate filtered datum 156 and/or subsequent filtered datum 156 using LLM 132.

With continued reference to FIG. 1, in some embodiments, processor 104 may generate filtered datum 156 as a function of patient data, cohort definition language data structure 160, user query datum 164 and one or more patient cohorts. In a non-limiting example, processor 104 may analyze patient data and user query datum 164 using a language processing module, finding at least a keyword and processor 104 may also classify patient data to one or more patient cohort and match with patient cohort reflected in cohort definition language data structure 160. Then, continuing the non-limiting example, processor 104 may transit through cohort definition language data structure 160 with the at least a keyword of patient data and user query datum 164 to find or generate filtered datum 156.

With continued reference to FIG. 1, in some embodiments, processor 104 may generate subsequent filtered datum as a function of filtered datum 156 and user request datum of user query datum 164 using cohort definition language data structure 160. For the purposes of this disclosure, a "user request datum" is a data element including a request that is made by a user related to a filtered datum. As a non-limiting example, user request datum may include a request of a user for additional or contextual information of filtered datum 156 displayed to a user. For example, and without limitation, if user query datum 164 includes 'when did this patient begin taking the drug?' and filtered datum 156 includes '12 months,' user request datum may include 'give me a detail.' For example, and without limitation, when user query datum 164 includes 'is this patient eligible for this clinical trial?' and filtered datum 156 includes 'no,' user request datum may include 'why?' In some embodiments, processor 104 may receive user request datum from remote device 124. In some embodiments, processor 104 may receive user request datum through chatbot.

With continued reference to FIG. 1, in one or more embodiments, apparatus 100 may include a display device communicatively connected to processor 104, wherein the display device may be configured to display filtered datum 156 and/or subsequent filtered datum. For the purposes of this disclosure, a "display device" is a device configured to show visual information. In some embodiments, computing device 104 may transmit filtered datum 156, subsequent filtered datum and/or cohort definition language data structure 160 to a display device (e.g., remote device 124). In some cases, display device may include a liquid crystal display (LCD), a cathode ray tube (CRT), a plasma display, a light emitting diode (LED) display, and any combinations thereof. Display device may include, but is not limited to, a smartphone, tablet, laptop, monitor, tablet, and the like. Display device may include a separate device that includes a transparent screen configured to display computer-generated images and/or information. In one or more embodiments, display device may be configured to visually present data through a user interface or a graphical user interface (GUI) to at least a user, wherein the user may interact with the data through the user interface or GUI, as described below. In one or more embodiments, a user may view GUI through display device. In one or more embodiments, display device may be located on a remote device, as described below. Additional details will be provided below in this disclosure through nonlimiting examples.

With continued reference to FIG. 1, display device may include a remote device 124. For the purposes of this disclosure, a "remote device" is a computer device separate and distinct from apparatus 100. For example, and without limitation, remote device 124 may include a smartphone, a tablet, a laptop, a desktop computer, or the like. In one or more embodiments, remote device 124 may be communicatively connected to apparatus 100 such as, for example, through network communication, through Bluetooth communication, and/or the like. In one or more embodiments, processor 104 may receive user query datum 164 and/or initiate one or more of subsequent steps through remote device 124. In one or more embodiments, one or more inputs from one or more users may be submitted through a user interface, such as a GUI, using remote device, as described below.

With continued reference to FIG. 1, for the purposes of this disclosure, a "user interface" is a means by which a user and a computer system interact, for example, using input devices and software. User interface may include a graphical user interface (GUI), command line interface (CLI), menu-driven user interface, touch user interface, voice user interface (VUI), form-based user interface, any combination thereof, or the like. In one or more embodiments, a user may interact with user interface using computing device distinct from and communicatively connected to processor 104 (i.e., a remote device), such as a smartphone, tablet, or the like operated by the user. User interface may include one or more graphical locator and/or cursor facilities allowing user to interact with graphical models and/or combinations thereof, for instance using a touchscreen, touchpad, mouse, keyboard, and/or other manual data entry device. For the purposes of this disclosure, a "graphical user interface (GUI)" is a type of user interface that allows end users to interact with electronic devices through visual representations. In one or more embodiments, GUI may include icons, menus, other visual indicators or representations (graphics), audio indicators such as primary notation, display information, and related user controls. Menu may contain a list of choices and may allow users to select one from them. A menu bar may be displayed horizontally across the screen as a pull-down menu. Menu may include a context menu that appears only when user performs a specific action. Files, programs, web pages, and the like may be represented using a small picture within GUI. In one or more embodiments, GUI may include a graphical visualization of a user profile and/or the like. In one or more embodiments, processor 104 may be configured to modify and/or update GUI as a function of at least an input or the like by populating a user interface data structure and visually presenting data through modification of the GUI.

With continued reference to FIG. 1, in one or more embodiments, GUI may contain one or more interactive elements. For the purposes of this disclosure, an "interactive element" is an element within GUI that allows for communication with processor 104 by one or more users. For example, and without limitation, interactive elements may include a plurality of tabs wherein selection of a particular tab, such as for example, by using a fingertip, may indicate to a system to perform a particular function and display the result through GUI. In one or more embodiments, interactive element may include tabs within GUI, wherein the selection of a particular tab may result in a particular function. In one or more embodiments, interactive elements may include words, phrases, illustrations, and the like to indicate a particular process that one or more users would like system to perform. A person of ordinary skill in the art, upon reviewing the entirety of this disclosure, will be aware of various ways in which user interfaces, GUIs, and/or elements thereof may be implemented and/or used as described in this disclosure. In some embodiments, user may manipulate remote device 124 to interact with cohort definition language data structure 160. In some embodiments, user may click or choose a node of tree diagram of cohort definition language data structure 160 to see information related to the node.

With continued reference to FIG. 1, in one or more embodiments, display device and/or remote device 124 may be configured to display at least an event handler graphic corresponding to at least an event handler. For the purposes of this disclosure, an "event handler graphic" is a graphical element with which user may interact using display device and/or remote device to enter data. Data may be entered, for instance and without limitation, for user query datum 164, or the like as described above. Event handler graphic may include, without limitation, a button, a link, a checkbox, a text entry box and/or window, a drop-down list, a slider, or any other event handler graphic deemed suitable by a person of ordinary skill in the art upon reviewing the entirety of this disclosure. For the purposes of this disclosure, an "event handler" is a module, data structure, function, and/or routine that performs an action on display device and/or remote device in response to one or more user inputs. For instance, and without limitation, event handler may record data corresponding to user selections of previously populated fields such as drop-down lists and/or text auto-complete and/or default entries, data corresponding to user selections of checkboxes, radio buttons, or the like, potentially along with automatically entered data triggered by such selections, user entry of textual data using a keyboard, touchscreen, speech-to-text program, or the like. Event handler may generate prompts for further information, may compare data to validation rules such as requirements that the data in question be entered within certain numerical ranges, and/or may modify data and/or generate warnings to user in response to such requirements. Event handler may convert data into expected and/or desired formats, for instance such as date formats, currency entry formats, name formats, or the like. Event handler may transmit data from a remote device to computing device.

With continued reference to FIG. 1, in one or more embodiments, event handler may include a cross-session state variable. For the purposes of this disclosure, a "cross-session state variable" is a variable recording data entered on remote device during a previous session. Such data may include, for instance, previously entered text, previous selections of one or more elements as described above, or the like. For instance, cross-session state variable data may represent a search that user entered in a past session. Cross-session state variable may be saved using any suitable combination of client-side data storage on remote device and server-side data storage on computing device; for instance, data may be saved wholly or in part as a "cookie" which may include data or an identification of remote device to prompt provision of cross-session state variable by the computing device, which may store the data on the computing device. Alternatively, or additionally, computing device may use login credentials, device identifier, and/or device fingerprint data to retrieve cross-session state variable, which the computing device may transmit to remote device. Cross-session state variable may include at least a prior session datum. A prior session datum may include any element of data that may be stored in cross-session state variable. Event handler graphic may be further configured to display at least a prior session datum, for instance and without limitation, by auto-populating user query data from previous sessions.

With continued reference to FIG. 1, in one or more embodiments, processor 104 and/or computing device may configure display device and/or remote device to generate a graphical view. For the purposes of this disclosure, a "graphical view" is a data structure that results in display of one or more graphical elements on a screen. Graphical view may include at least a display element. For the purposes of this disclosure, a "display element" is an image that a program and/or data structure may cause to be displayed. Display elements may include, without limitation, windows, pop-up boxes, web browser pages, display layers, and/or any other display element deemed relevant by a person of ordinary skill in the art upon reviewing the entirety of this disclosure. Graphical view may include at least a selectable event graphic corresponding to one or more selectable event handlers. For the purposes of this disclosure, a "selectable event graphic" is a graphical element that, upon selection, will trigger an action to be performed. Selection may be performed using a cursor or other locator as manipulated using a locator device such as a mouse, touchscreen, track pad, joystick, or the like. As a nonlimiting example, a selectable event graphic may include a redirection link, defined as a hyperlink, button, image, portion of an image, and/or other graphic containing or referring to a uniform resource locator (URL) and/or other resource locator to another graphical view including without limitation buttons, and/or to a process that performs navigation to such URL and/or other resource locator upon selection of selectable event graphic. Redirection may be performed using any event handler, including without limitation event handlers detecting the click of a mouse or other locator, access of redirection link using a touchscreen, the selection of any key, mouseover events, or the like.

Figure 2:
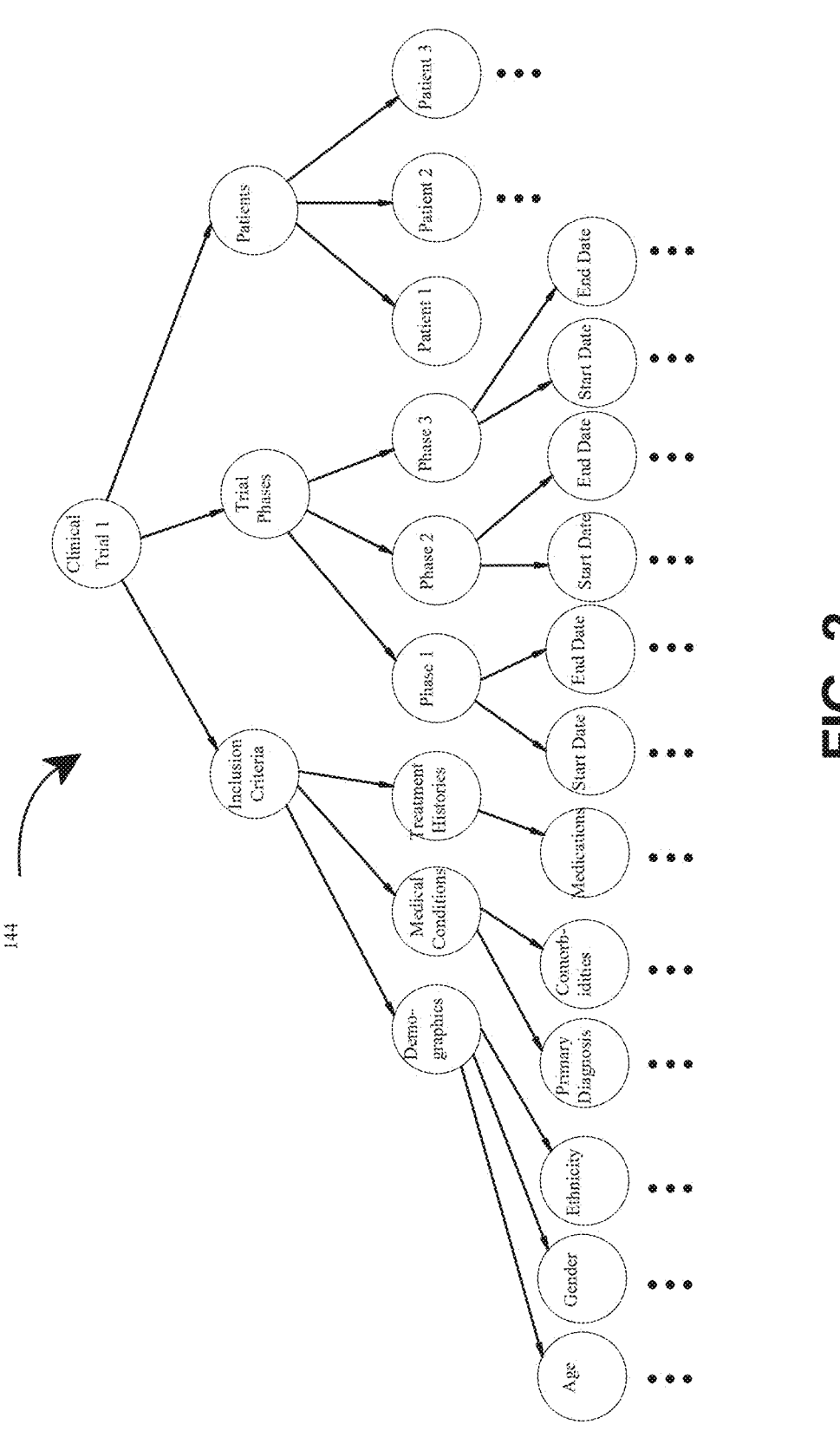
FIG. 2 illustrates a configuration of an exemplary cohort definition language data structure.

Referring now to FIG. 2, a configuration of an exemplary cohort definition language data structure 160 is illustrated. In a non-limiting example, cohort definition language data structure 160 may include a formal, standardized framework used to specify the attributes, inclusion/exclusion criteria, and logical conditions necessary to define a group of patients (a cohort) for analytical or clinical purposes. For example, and without limitation, cohort definition language data structure 160 may include a standardized framework used to specify criteria for specific clinical trial. For example, and without limitation, cohort definition language data structure 160 may include a standardized framework of medications and treatments for a cohort of patients.

With continued reference to FIG. 1, as a non-limiting example, cohort definition language data structure 160 may include a tree diagram. FIG. 2 illustrates a portion of tree diagram of cohort definition language data structure 160. For the purposes of this disclosure, a "tree diagram" is a graphical representation of hierarchical data using nodes (points or vertices) connected by edges (lines or branches). As a non-limiting example, each node of tree diagram may include different information from the analysis of note data 112 and each node is connected to the others by correlations of keywords from note data 112. In some embodiments, node of tree diagram may include temporal element 116. For example, and without limitation, node may include start date and end date of trial phases of clinical trial as shown in FIG.

2. For example, and without limitation, node may include the time and date when a user taken medication (not shown in FIG. 2).

With continued reference to FIG. 2, as another non-limiting example, cohort definition language data structure 160 may include a JavaScript Object Notation (JSON) format. For example, and without limitation, cohort definition language data structure 160 may include {"id": "med123", "name": "John Doe", "dose": "10 mg", "route": "oral", "frequency": "once daily", "startDate": "2023 Jan. 1", "endDate": "2023 Dec. 31", "prescribingDoctor": {"id": "doc456", "name": "Dr. Smith"}}. Cohort definition language data structure 160 may be a representation of a plurality of data associated with note data 112 and/or textual outputs. Cohort definition language data structure 160 may include a parametric map that takes high dimensional raw data and abstracts it into a lower dimensional feature vector that ideally encapsulates the essential information. Cohort definition language data structure 160 may involve linking or integrating note data 112 and/or textual outputs with the descriptive or explanatory multi-modal data to provide additional context, enhance understanding, and convey relevant information. In an embodiment, cohort definition language data structure 160 may include a relationship or connection between note data 112 and/or textual outputs. In another embodiment, cohort definition language data structure 160 may include a relationship or connection between note data 112 and/or textual outputs. Cohort definition language data structure 160 may include a longitudinal record of a patient's health history. By linking note data 112 and/or textual outputs to each other, processor 104 can track and analyze the cardiac relationships of note data 112 and/or textual outputs. This longitudinal perspective enables the identification of trends, changes, or patterns in note data 112 and/or textual outputs.

With continued reference to FIG. 2, in some embodiments, processor 104 may generate a plurality of cohort definition language data structures 160 and each of the plurality of cohort definition language data structures 160 may include different analytical or clinical purpose. As a non-limiting example, first cohort definition language data structure may be related to a first clinical trial and second cohort definition language data structure may be related to a second clinical trial. As another non-limiting example, first cohort definition language data structure may be related to a first patient and second cohort definition language data structure may be related to a second patient. In some embodiments, processor 104 may generate cohort definition language data structure 160 as a function of temporal element 116 of note data 112. As a non-limiting example, each layer of decision tree of the cohort definition language data structure 160 may represent different sequential dates. For instance, the first layer could correspond to the most recent timeline, while subsequent layers could reflect progressively later timelines. In a non-limiting example, the first layer could correspond to the most recently administered medication or medical treatment, with subsequent layers reflecting progressively earlier instances. In some embodiments, each node of decision tree of cohort definition language data structure 160 may include temporal element 116.

With continued reference to FIG. 2, cohort definition language data structure 160 may be represented in vector form. A vector representing cohort definition language data structure 160 is a mathematical construct that can be used to represent multiple data points or variables. In the context of healthcare or any other domain, a vector can be constructed to capture and represent a diverse set of data points. A vector has a certain number of dimensions, which may correspond to the number of data points or variables being represented. Each dimension in the vector corresponds to a specific data point or variable. Each dimension in the vector represents a distinct data point or variable. For example, in the healthcare domain, these data points could include patient demographics (e.g., age, gender), medical history (e.g., conditions, medications, surgeries), laboratory results (e.g., cholesterol levels, glucose levels), vital signs (e.g., blood pressure, heart rate), clinical trial histories, or any other relevant healthcare-related information. Values within each dimension of the vector, there are corresponding values that represent the specific data point or variable. These values can be numerical, categorical, or symbolic, depending on the nature of the data being represented. In an embodiment, cohort definition language data structure 160 represented as a vector may be used to convey a large amount of information regarding the patient. This may include information regarding note data 112 and/or textual outputs, and the like. In a non-limiting example, a cohort definition language data structure 160 in vector form may represent all or part of medications, surgeries, treatments, and the like that a patient has had. Additionally, a cohort definition language data structure 160 in vector form may represent all or part of patient demographics, medical history, past and present diagnosis, past and present medical procedures, medications, laboratory results, clinical notes.

Figure 3:
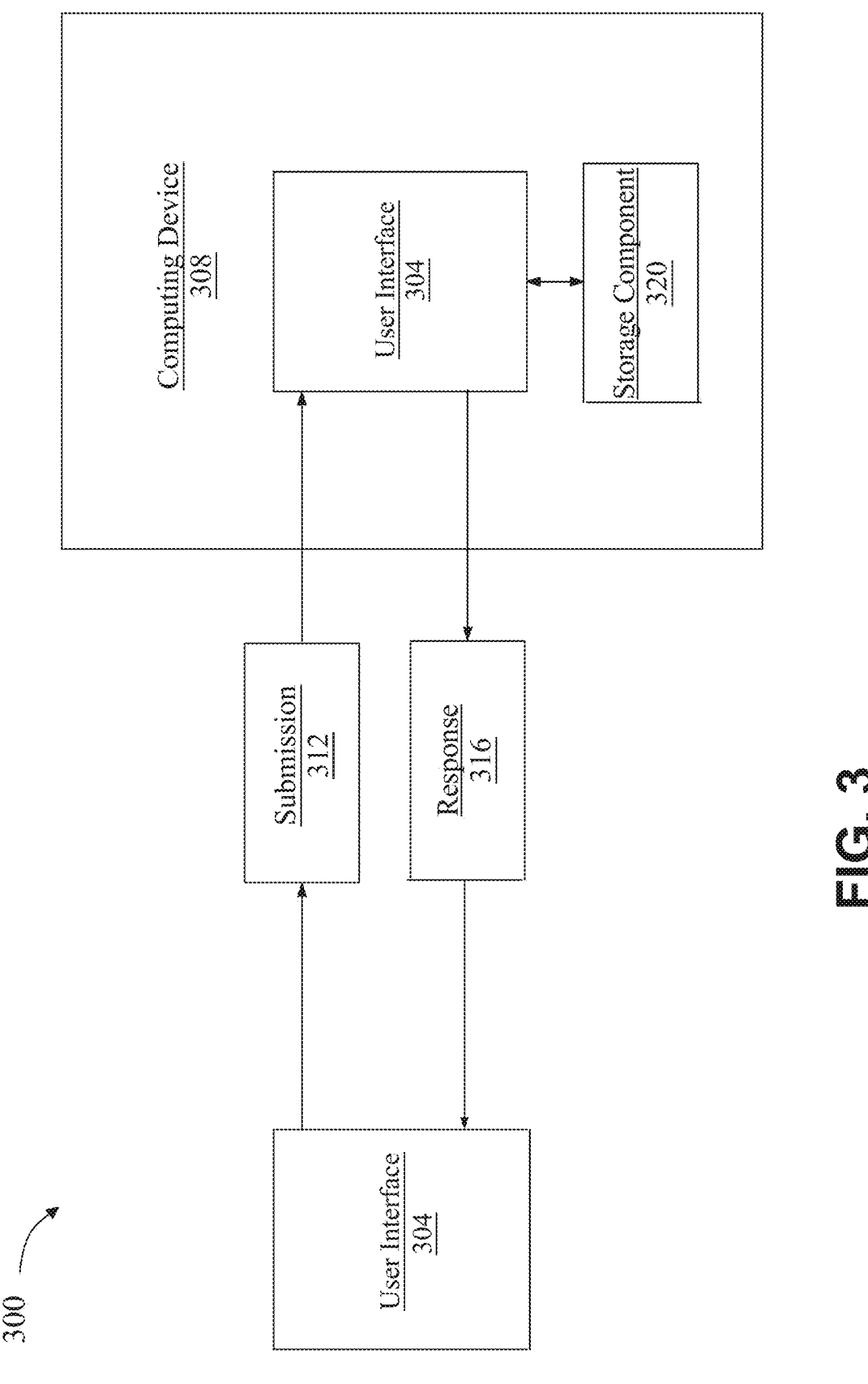
FIG. 3 illustrates a block diagram of an exemplary chatbot system.

Referring to FIG. 3, a chatbot system 300 is schematically illustrated. According to some embodiments, a user interface 304 may be communicative with a computing device 303 that is configured to operate a chatbot. In some cases, user interface 304 may be local to computing device 303. Alternatively or additionally, in some cases, user interface 304 may remote to computing device 303 and communicative with the computing device 303, by way of one or more networks, such as without limitation the internet. Alternatively or additionally, user interface 304 may communicate with user device 303 using telephonic devices and networks, such as without limitation fax machines, short message service (SMS), or multimedia message service (MMS). Commonly, user interface 304 communicates with computing device 303 using text-based communication, for example without limitation using a character encoding protocol, such as American Standard for Information Interchange (ASCII). Typically, a user interface 304 conversationally interfaces a chatbot, by way of at least a submission 312, from the user interface 303 to the chatbot, and a response 316, from the chatbot to the user interface 304. In many cases, one or both of submission 312 and response 316 are text-based communication. Alternatively or additionally, in some cases, one or both of submission 312 and response 316 are audio-based communication.

Continuing in reference to FIG. 3, a submission 312 once received by computing device 303 operating a chatbot, may be processed by a processor. In some embodiments, processor processes a submission 312 using one or more of keyword recognition, pattern matching, and natural language processing. In some embodiments, processor employs real-time learning with evolutionary algorithms. In some cases, processor may retrieve a pre-prepared response from at least a storage component 320, based upon submission 312. Alternatively or additionally, in some embodiments, processor communicates a response 316 without first receiving a submission 312, thereby initiating conversation. In some cases, processor communicates an inquiry to user interface 304; and the processor is configured to process an answer to the inquiry in a following submission 312 from the user interface 304. In some cases, an answer to an inquiry present within a submission 312 from a user device 304 may be used by computing device 303 as an input to another function.

With continued reference to FIG. 3, a chatbot may be configured to provide a user with a plurality of options as an input into the chatbot. Chatbot entries may include multiple choice, short answer response, true or false responses, and the like. A user may decide on what type of chatbot entries are appropriate. In some embodiments, the chatbot may be configured to allow the user to input a freeform response into the chatbot. The chatbot may then use a decision tree, data base, or other data structure to respond to the users entry into the chatbot as a function of a chatbot input. As used in the current disclosure, "chatbot input" is any response that a user inputs in to a chatbot as a response to a prompt or question. As a non-limiting example, chatbot input may include patient data, user query datum, and the like.

With continuing reference to FIG. 3, computing device 303 may be configured to the respond to a chatbot input using a decision tree. A "decision tree," as used in this disclosure, is a data structure that represents and combines one or more determinations or other computations based on and/or concerning data provided thereto, as well as earlier such determinations or calculations, as nodes of a tree data structure where inputs of some nodes are connected to outputs of others. Decision tree may have at least a root node, or node that receives data input to the decision tree, corresponding to at least a candidate input into a chatbot. Decision tree has at least a terminal node, which may alternatively or additionally be referred to herein as a "leaf node," corresponding to at least an exit indication; in other words, decision and/or determinations produced by decision tree may be output at the at least a terminal node. Decision tree may include one or more internal nodes, defined as nodes connecting outputs of root nodes to inputs of terminal nodes. Computing device 303 may generate two or more decision trees, which may overlap; for instance, a root node of one tree may connect to and/or receive output from one or more terminal nodes of another tree, intermediate nodes of one tree may be shared with another tree, or the like.

Still referring to FIG. 3, computing device 303 may build decision tree by following relational identification; for example, relational indication may specify that a first rule module receives an input from at least a second rule module and generates an output to at least a third rule module, and so forth, which may indicate to computing device 303 an in which such rule modules will be placed in decision tree. Building decision tree may include recursively performing mapping of execution results output by one tree and/or subtree to root nodes of another tree and/or subtree, for instance by using such execution results as execution parameters of a subtree. In this manner, computing device 303 may generate connections and/or combinations of one or more trees to one another to define overlaps and/or combinations into larger trees and/or combinations thereof. Such connections and/or combinations may be displayed by visual interface to user, for instance in first view, to enable viewing, editing, selection, and/or deletion by user; connections and/or combinations generated thereby may be highlighted, for instance using a different color, a label, and/or other form of emphasis aiding in identification by a user. In some embodiments, subtrees, previously constructed trees, and/or entire data structures may be represented and/or converted to rule modules, with graphical models representing them, and which may then be used in further iterations or steps of generation of decision tree and/or data structure. Alternatively or additionally subtrees, previously constructed trees, and/or entire data structures may be converted to APIs to interface with further iterations or steps of methods as described in this disclosure. As a further example, such subtrees, previously constructed trees, and/or entire data structures may become remote resources to which further iterations or steps of data structures and/or decision trees may transmit data and from which further iterations or steps of generation of data structure receive data, for instance as part of a decision in a given decision tree node.

Continuing to refer to FIG. 3, decision tree may incorporate one or more manually entered or otherwise provided decision criteria. Decision tree may incorporate one or more decision criteria using an application programmer interface (API). Decision tree may establish a link to a remote decision module, device, system, or the like. Decision tree may perform one or more database lookups and/or look-up table lookups. Decision tree may include at least a decision calculation module, which may be imported via an API, by incorporation of a program module in source code, executable, or other form, and/or linked to a given node by establishing a communication interface with one or more exterior processes, programs, systems, remote devices, or the like; for instance, where a user operating system has a previously existent calculation and/or decision engine configured to make a decision corresponding to a given node, for instance and without limitation using one or more elements of domain knowledge, by receiving an input and producing an output representing a decision, a node may be configured to provide data to the input and receive the output representing the decision, based upon which the node may perform its decision.

Figure 4:
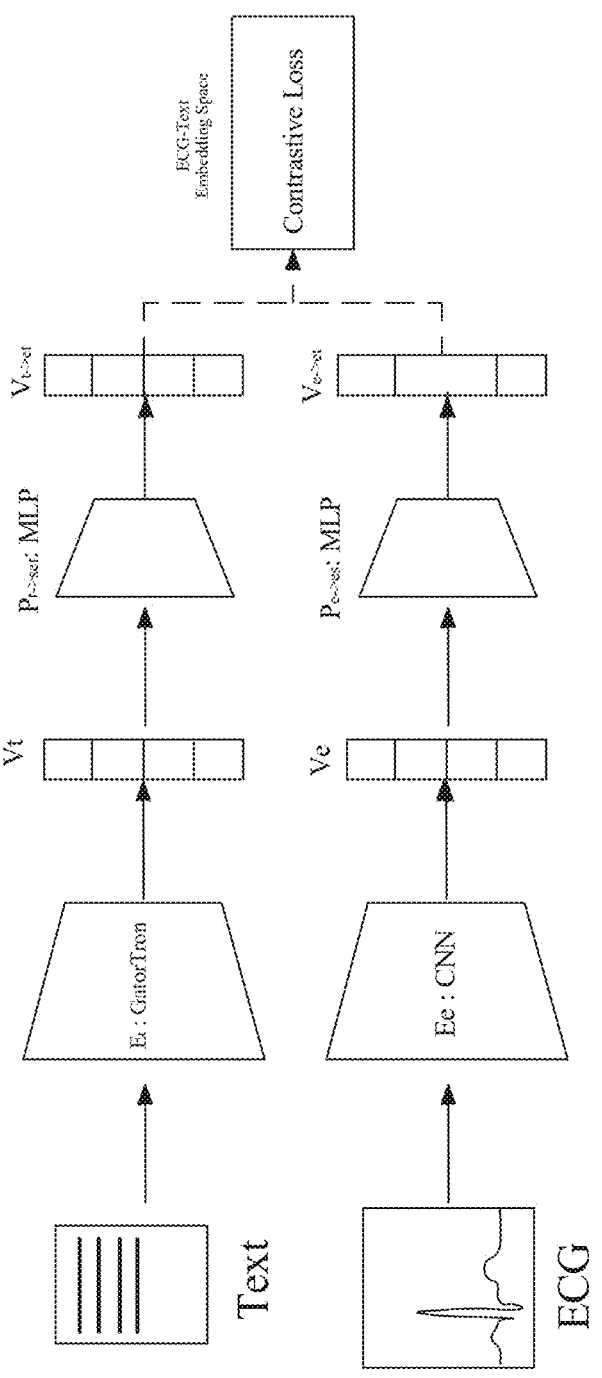
FIG. 4 illustrates a diagram of an exemplary Contrastive Visual Representation Learning from Text (ConVIRT) model.

Now referring to FIG. 4, an exemplary embodiment of ConVIRT model that can be used to analyze note data 112 and generate cohort definition language data structure 160 is illustrated. Processor 104 may take a plurality of note data 112 that have an association with at least 50 patients and are considered in the vocabulary. In some cases, processor 104 may do a mapping of note data 112 to maintain the same phenotypic information. To create cohort definition language data structure 160, processor 104 may randomly select one note data 112 related to a given patient's timeline. In the ECG-Text model, processor 104 may pair electrocardiogram signals with unstructured text data obtained from a variety of medical sources, including ECG reports, ECHO reports, pathology reports, radiology reports, microbiology reports and clinical documents. These may be collectively referred to as note data 112. Processor 104 may apply the contrastive learning between ECG and Text in joint ECG-Text Embedding space $\Omega_{et}$ $$v_e^i = E_e(x_e^i)$$

$$v_t^i = E_t(x_t^i)$$

$$v_{e-et}^i = P_{e \to et}(v_e^i)$$

$$v_{s-et}^i = P_{s \to et}(v_t^i)$$

In an embodiment, $L_{et}$ be the contrastive loss between ECG and Text, $$L_i^{e \to t}$$

be the contrastive loss directed from ECG to Text, and $$L_i^{t \to e}$$

be the contrastive loss directed from Text to ECG. Then, the loss for the ECG-Text model is given by:

$$L_{et} = \frac{1}{n} \sum_{i=1}^{N} (\lambda_{et} L_i^{e \to t} + (1 - \lambda_{et}) L_i^{t \to e})$$

$$L_i^{s \to t} = -\log \frac{\exp\left(s\left(v_{e-et}^i, v_{t-et}^i\right)/T\right)}{\sum_{K=1}^{N} \exp\left(s\left(v_{e-et}^i, v_{t-et}^k\right)/T\right)}$$

Counts for ECGs and unique patients for each downstream task cohort.

$$L_i^{t \to e} = -\log \frac{\exp\left(s\left(v_{t-et}^i, v_{e-et}^i\right)/T\right)}{\sum_{K=1}^{N} \exp\left(s\left(v_{t-et}^i, v_{e-et}^k\right)/T\right)}$$

Figure 5:
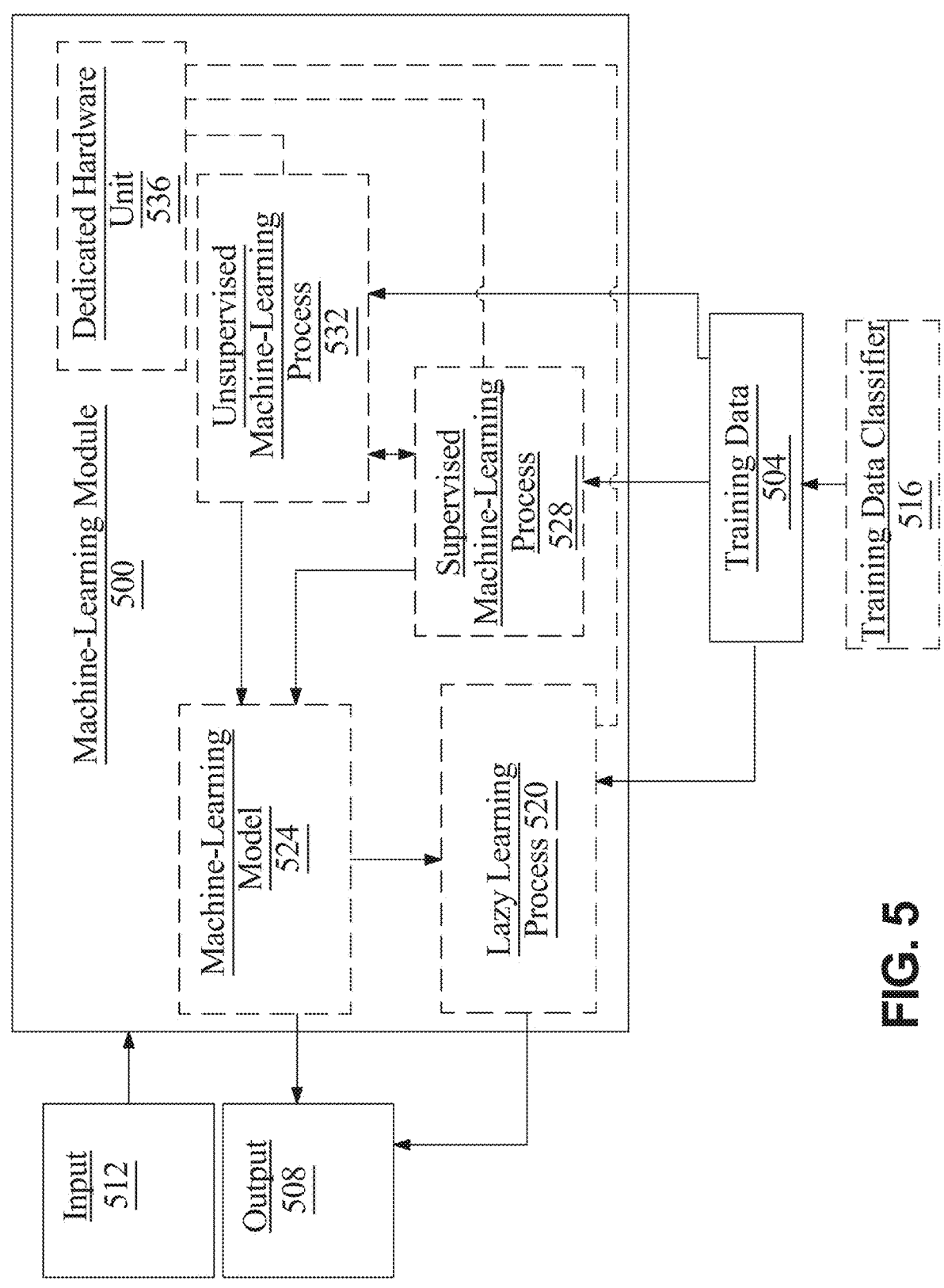
FIG. 5 illustrates a block diagram of an exemplary machine-learning module.

Referring now to FIG. 5, an exemplary embodiment of a machine-learning module 500 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 504 to generate an algorithm instantiated in hardware or software logic, data structures, and/or functions that will be performed by a computing device/module to produce outputs 508 given data provided as inputs 512; this is in contrast to a non-machine learning software program where the commands to be executed are determined in advance by a user and written in a programming language.

Still referring to FIG. 5, "training data," as used herein, is data containing correlations that a machine-learning process may use to model relationships between two or more categories of data elements. For instance, and without limitation, training data 504 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 504 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 504 according to various correlations; correlations may indicate causative and/or predictive links between categories of data elements, which may be modeled as relationships such as mathematical relationships by machine-learning processes as described in further detail below. Training data 504 may be formatted and/or organized by categories of data elements, for instance by associating data elements with one or more descriptors corresponding to categories of data elements. As a non-limiting example, training data 504 may include data entered in standardized forms by persons or processes, such that entry of a given data element in a given field in a form may be mapped to one or more descriptors of categories. Elements in training data 504 may be linked to descriptors of categories by tags, tokens, or other data elements; for instance, and without limitation, training data 504 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 5, training data 504 may include one or more elements that are not categorized; that is, training data 504 may not be formatted or contain descriptors for some elements of data. Machine-learning algorithms and/or other processes may sort training data 504 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 504 to be made applicable for two or more distinct machine-learning algorithms as described in further detail below. Training data 504 used by machine-learning module 500 may correlate any input data as described in this disclosure to any output data as described in this disclosure. As a non-limiting illustrative example, input data may include note data 112, textual output, user query datum 164, and the like. As a non-limiting illustrative example, output data may include textual output, cohort definition language data structure 160, filtered datum 156, and the like.

Further referring to FIG. 5, training data may be filtered, sorted, and/or selected using one or more supervised and/or unsupervised machine-learning processes and/or models as described in further detail below; such models may include without limitation a training data classifier 516. Training data classifier 516 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 500 may generate a classifier using a classification algorithm, defined as a processes whereby a computing device and/or any module and/or component operating thereon derives a classifier from training data 504. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 516 may classify elements of training data to patient cohorts. For example, and without limitation, training data classifier 516 may classify elements of training data to cohorts of patient's age, gender, weight, lifestyle, and the like.

Still referring to FIG. 5, Computing device may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A)$ $P(A)=P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Computing device may then calculate a likelihood table by calculating probabilities of different data entries and classification labels. Computing device may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 5, Computing device may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 5, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute/as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

With further reference to FIG. 5, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Continuing to refer to FIG. 5, computer, processor, and/or module may be configured to preprocess training data. "Preprocessing" training data, as used in this disclosure, is transforming training data from raw form to a format that can be used for training a machine learning model. Preprocessing may include sanitizing, feature selection, feature scaling, data augmentation and the like.

Still referring to FIG. 5, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively or additionally, one or more training examples may be identified as having poor quality data, where "poor quality" is defined as having a signal to noise ratio below a threshold value. Sanitizing may include steps such as removing duplicative or otherwise redundant data, interpolating missing data, correcting data errors, standardizing data, identifying outliers, and the like. In a nonlimiting example, sanitization may include utilizing algorithms for identifying duplicate entries or spell-check algorithms.

As a non-limiting example, and with further reference to FIG. 5, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 5, computing device, processor, and/or module may be configured to precondition one or more training examples. For instance, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units.

In some embodiments, and with continued reference to FIG. 5, computing device, processor, and/or module may down-sample elements of a training example to a desired lower number of data elements. As a non-limiting example, a high pixel count image may have 256 pixels, however a desired number of pixels may be 128. Processor may down-sample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean up side-effects of compression.

Further referring to FIG. 5, feature selection includes narrowing and/or filtering training data to exclude features and/or elements, or training data including such elements, that are not relevant to a purpose for which a trained machine-learning model and/or algorithm is being trained, and/or collection of features and/or elements, or training data including such elements, on the basis of relevance or utility for an intended task or purpose for a trained machine-learning model and/or algorithm is being trained. Feature selection may be implemented, without limitation, using any process described in this disclosure, including without limitation using training data classifiers, exclusion of outliers, or the like.

With continued reference to FIG. 5, feature scaling may include, without limitation, normalization of data entries, which may be accomplished by dividing numerical fields by norms thereof, for instance as performed for vector normalization. Feature scaling may include absolute maximum scaling, wherein each quantitative datum is divided by the maximum absolute value of all quantitative data of a set or subset of quantitative data. Feature scaling may include min-max scaling, in which each value X has a minimum value $X_{min}$ in a set or subset of values subtracted therefrom, with the result divided by the range of the values, give maximum value in the set or subset $$X_{max}: X_{new} = \frac{X - X_{min}}{X_{max} - X_{min}}.$$

Feature scaling may include mean normalization, which involves use of a mean value of a set and/or subset of values, $X_{mean}$ with maximum and minimum values:

$$X_{new} = \frac{X - X_{mean}}{X_{max} - X_{min}}.$$

Feature scaling may include standardization, where a difference between X and $X_{mean}$ is divided by a standard deviation σ of a set or subset of values:

$$X_{new} = \frac{X - X_{mean}}{\sigma}.$$

Scaling may be performed using a median value of a set or subset $X_{median}$ and/or interquartile range (IQR), which represents the difference between the $25^{th}$ percentile value and the $50^{th}$ percentile value (or closest values thereto by a rounding protocol), such as:

$$X_{new} = \frac{X - X_{median}}{IQR}.$$

Persons skilled in the art, upon reviewing the entirety of this disclosure, will be aware of various alternative or additional approaches that may be used for feature scaling.

Further referring to FIG. 5, computing device, processor, and/or module may be configured to perform one or more processes of data augmentation. "Data augmentation" as used in this disclosure is addition of data to a training set using elements and/or entries already in the dataset. Data augmentation may be accomplished, without limitation, using interpolation, generation of modified copies of existing entries and/or examples, and/or one or more generative AI processes, for instance using deep neural networks and/or generative adversarial networks; generative processes may be referred to alternatively in this context as "data synthesis" and as creating "synthetic data." Augmentation may include performing one or more transformations on data, such as geometric, color space, affine, brightness, cropping, and/or contrast transformations of images.

Still referring to FIG. 5, machine-learning module 500 may be configured to perform a lazy-learning process 520 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 504. Heuristic may include selecting some number of highest-ranking associations and/or training data 504 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 5, machine-learning processes as described in this disclosure may be used to generate machine-learning models 524. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 524 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 524 may be generated by creating an artificial neural network, such as a convolutional neural network comprising an input layer of nodes, one or more intermediate layers, and an output layer of nodes. Connections between nodes may be created via the process of "training" the network, in which elements from a training data 504 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 5, machine-learning algorithms may include at least a supervised machine-learning process 528. At least a supervised machine-learning process 528, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include note data 112, textual output, user query datum 164, and the like as described above as inputs, textual output, cohort definition language data structure 160, filtered datum 156, and the like as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 504. Persons skilled in the art, upon reviewing the entirety of this disclosure, will be aware of various possible variations of at least a supervised machine-learning process 528 that may be used to determine relation between inputs and outputs. Supervised machine-learning processes may include classification algorithms as defined above.

With further reference to FIG. 5, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms.

Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 5, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 5, machine learning processes may include at least an unsupervised machine-learning processes 532. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 532 may not require a response variable; unsupervised processes 532 may be used to find interesting patterns and/or inferences between variables, to determine a degree of correlation between two or more variables, or the like.

Still referring to FIG. 5, machine-learning module 500 may be designed and configured to create a machine-learning model 524 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 5, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 5, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 5, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 5, retraining and/or additional training may be performed using any process for training described above, using any currently or previously deployed version of a machine-learning model and/or algorithm as a starting point. Training data for retraining may be collected, preconditioned, sorted, classified, sanitized or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 5, one or more processes or algorithms described above may be performed by at least a dedicated hardware unit 536. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 536 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 536 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 536 to perform one or more operations described herein, such as evaluation of model and/or algorithm outputs, one-time or iterative updates to parameters, coefficients, weights, and/or biases, and/or any other operations such as vector and/or matrix operations as described in this disclosure.

Figure 6:
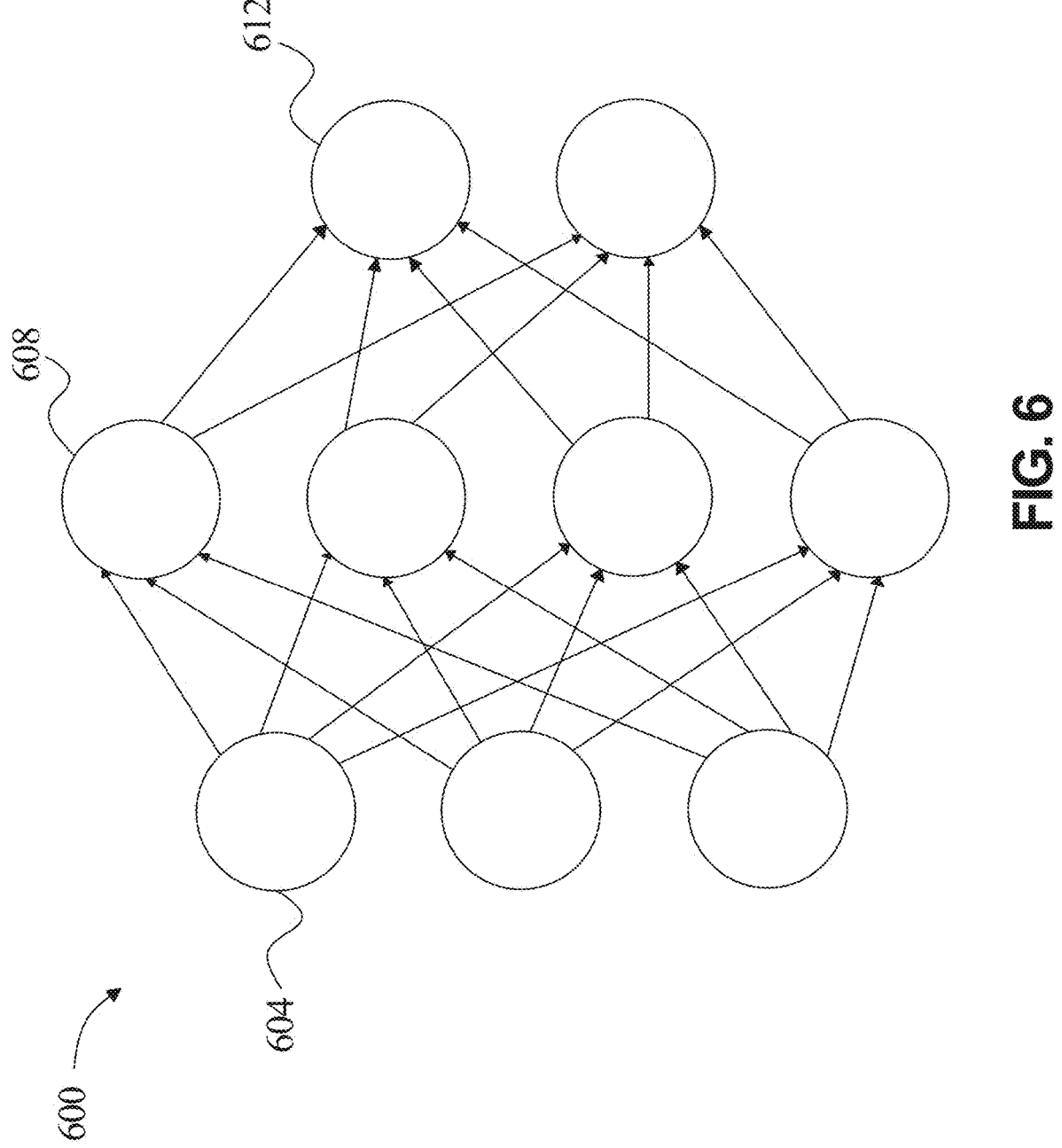
FIG. 6 illustrates a diagram of an exemplary nodal neural network.

Referring now to FIG. 6, an exemplary embodiment of neural network 600 is illustrated. A neural network 600 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 604, one or more intermediate layers 608, and an output layer of nodes 612. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network, or may feed outputs of one layer back to inputs of the same or a different layer in a "recurrent network". As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 7:
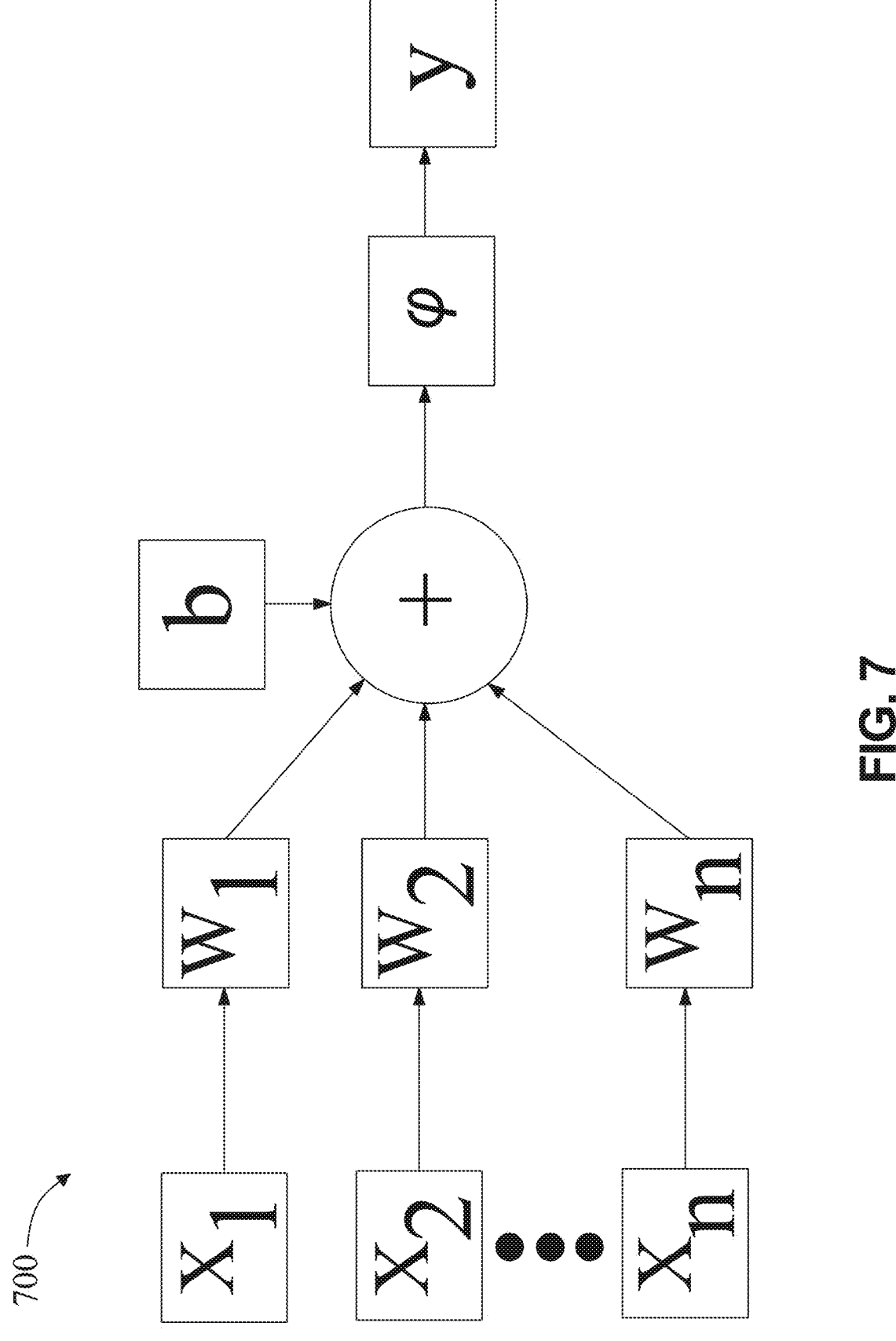
FIG. 7 illustrates a block diagram of an exemplary node in a neural network.

Referring now to FIG. 7, an exemplary embodiment of a node 700 of a neural network is illustrated. A node may include, without limitation a plurality of inputs $x_i$ that may receive numerical values from inputs to a neural network containing the node and/or from other nodes. Node may perform one or more activation functions to produce its output given one or more inputs, such as without limitation computing a binary step function comparing an input to a threshold value and outputting either a logic 1 or logic 0 output or something equivalent, a linear activation function whereby an output is directly proportional to the input, and/or a non-linear activation function, wherein the output is not proportional to the input. Non-linear activation functions may include, without limitation, a sigmoid function of the form $$f(x) = \frac{1}{1 - e^{-x}}$$

given input x, a tanh (hyperbolic tangent) function, of the form $$\frac{e^x - e^{-x}}{e^x + e^{-x}},$$

a tanh derivative function such as $f(x) = \tan h^2(x)$, a rectified linear unit function such as $f(x) = \max(0, x)$, a "leaky" and/or "parametric" rectified linear unit function such as $f(x) = \max(ax, x)$ for some a, an exponential linear units function such as $$f(x) = \begin{cases} x \text{ for } x \geq 0 \\ \alpha(e^x - 1) \text{ for } x < 0 \end{cases}$$

for some value of $\alpha$ (this function may be replaced and/or weighted by its own derivative in some embodiments), a softmax function such as $$f(x_i) = \frac{e^x}{\sum_i x_i}$$

where the inputs to an instant layer are $x_i$, a swish function such as $f(x) = x*\text{sigmoid}(x)$, a Gaussian error linear unit function such as $f(x) = a(1 + \tan h(\sqrt{2/\pi}(x + bx^r)))$ for some values of a, b, and r, and/or a scaled exponential linear unit function such as $$f(x) = \lambda \begin{cases} \alpha(e^x - 1) \text{ for } x < 0 \\ x \text{ for } x \geq 0 \end{cases}.$$

Fundamentally, there is no limit to the nature of functions of inputs $x_i$ that may be used as activation functions. As a non-limiting and illustrative example, node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function φ, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Figure 8:
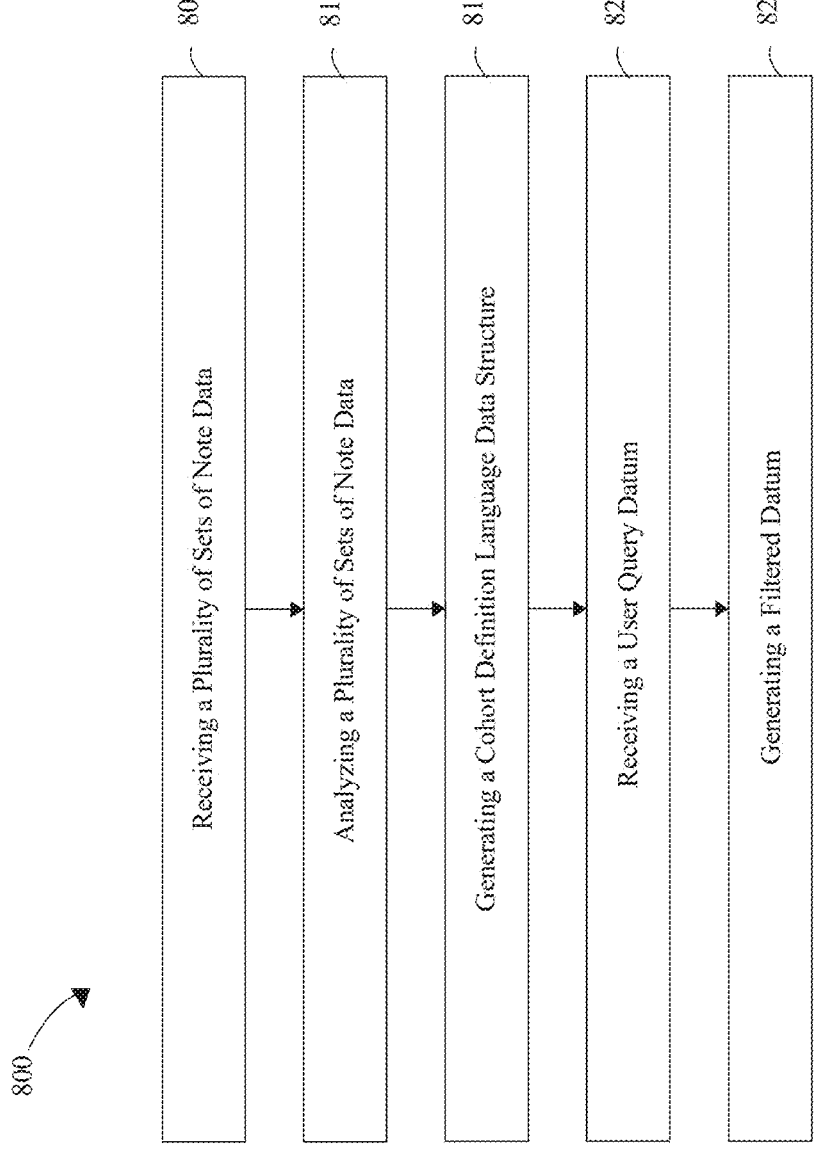
FIG. 8 illustrates a flow diagram of an exemplary method for responding to a user query by generating a data structure.

Referring now to FIG. 8, a flow diagram of an exemplary method 800 for responding to a user query by generating a data structure is illustrated. The method 800 contains a step 805 of receiving, using at least a processor, a plurality of sets of note data, wherein the plurality of sets of note data includes at least a temporal element. This may be implemented as referenced to FIGS. 1-7.

With continued reference to FIG. 8, method 800 contains a step 810 of analyzing, using at least a processor, a plurality of sets of note data using a machine-learning module, wherein the machine-learning module includes a large language model. In some embodiments, analyzing the plurality of sets of note data using the machine-learning module may include generating language training data, wherein the language training data may include exemplary note data and exemplary textual outputs, training the large language model using the language training data and analyzing the plurality of note data using the trained large language model. In some embodiments, analyzing the plurality of sets of note data using the machine-learning module may include iteratively training the large language model as a function of previous iterations. In some embodiments, analyzing the plurality of sets of note data using the machine-learning module may include generating cohort training data, wherein the cohort training data may include correlations between exemplary note data and exemplary patient cohorts, training a cohort classifier using the cohort training data and classifying the plurality of note data into one or more patient cohorts using trained cohort classifier. In some embodiments, analyzing the plurality of sets of note data may include analyzing the plurality of sets of note data using a Contrastive Visual Representation Learning from Text (ConVIRT) model of the machine-learning module. These may be implemented as referenced to FIGS. 1-7.

With continued reference to FIG. 8, method 800 contains a step 815 of generating, using at least a processor, a cohort definition language data structure as a function of an analysis. In some embodiments, the cohort definition language data structure may include a JavaScript Object Notation (JSON) format. These may be implemented as referenced to FIGS. 1-7.

With continued reference to FIG. 8, method 800 contains a step 820 of receiving, using at least a processor, a user query datum. These may be implemented as referenced to FIGS. 1-7.

With continued reference to FIG. 8, method 800 contains a step 825 of generating, using at least a processor, a filtered datum as a function of the cohort definition language data structure and the user query datum. In some embodiments, generating the filtered datum may include receiving patient data and generating the filtered datum as a function of the patient data, the cohort definition language data structure, the user query datum and the one or more patient cohorts. In some embodiments, generating the filtered datum may include generating a subsequent filtered datum as a function of the filtered datum and a user request datum using the cohort definition language data structure. In some embodiments, method 800 may further include retrieving, using the at least a processor, health record data from a note database as a function of a set of filtered temporal criteria of the filtered datum, wherein the set of filtered temporal criteria may be related to a plurality of temporal criteria related to a time of treatment of the cohort definition language data structure. In some embodiments, method 800 may further include transmitting the filtered datum to a remote device. These may be implemented as referenced to FIGS. 1-7.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 9:
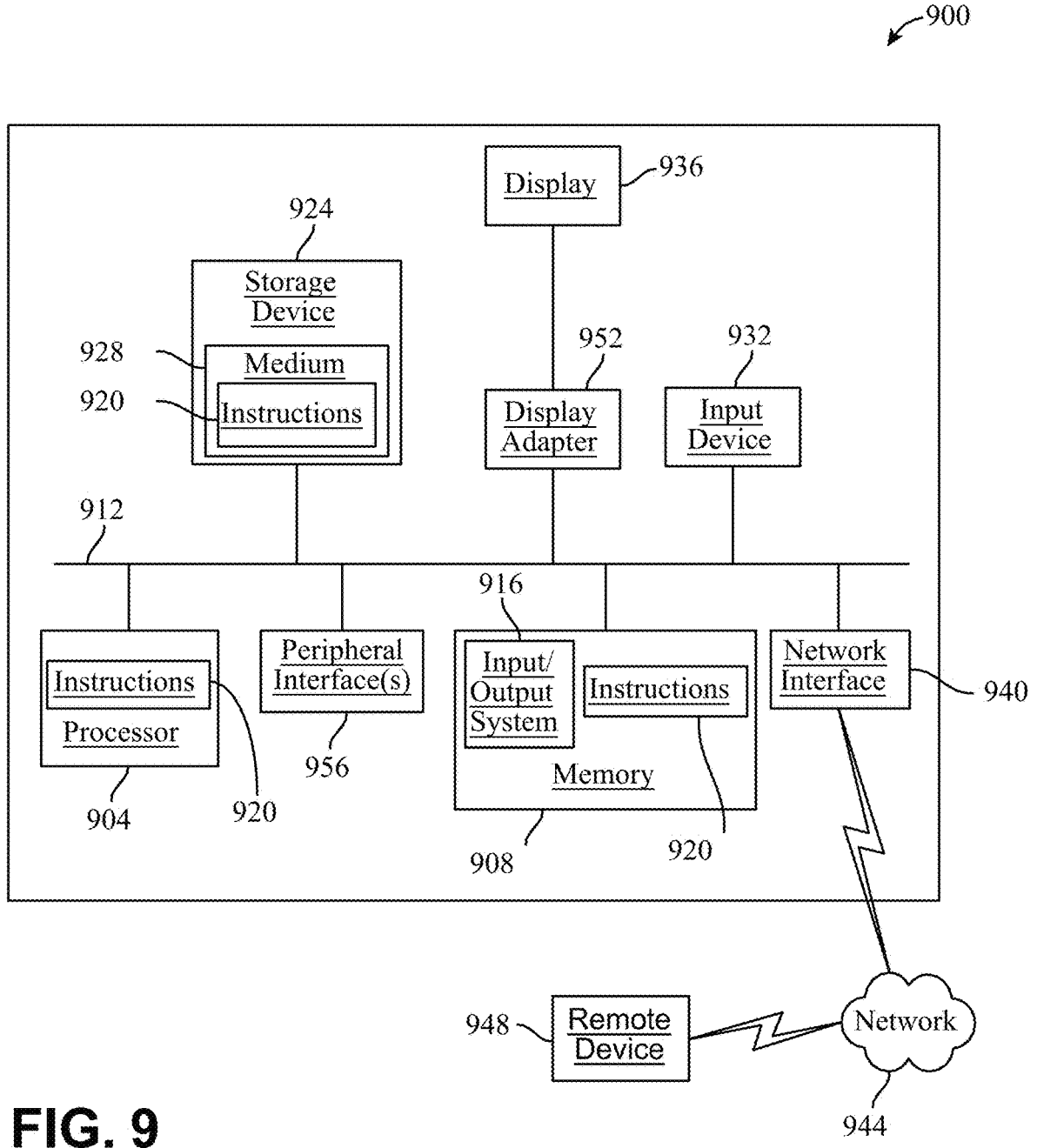
FIG. 9 illustrates a block diagram of a computing system that can be used to implement any one or more of the methodologies disclosed herein and any one or more portions thereof.

FIG. 9 shows a diagrammatic representation of one embodiment of a computing device in the exemplary form of a computer system 900 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 900 includes a processor 904 and memory 908 that communicate with each other, and with other components, via a bus 912. Bus 912 may include any of several types of bus structures including, but not limited to, memory bus, memory controller, a peripheral bus, a local bus, and any combinations thereof, using any of a variety of bus architectures.

Processor 904 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 904 may be organized according to Von Neumann and/or Harvard architecture as a non-limiting example. Processor 904 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 908 may include various components (e.g., machine-readable media) including, but not limited to, a random-access memory component, a read only component, and any combinations thereof. In one example, a basic input/output system 916 (BIOS), including basic routines that help to transfer information between elements within computer system 900, such as during start-up, may be stored in memory 908. Memory 908 may also include (e.g., stored on one or more machine-readable media) instructions (e.g., software) 920 embodying any one or more of the aspects and/or methodologies of the present disclosure. In another example, memory 908 may further include any number of program modules including, but not limited to, an operating system, one or more application programs, other program modules, program data, and any combinations thereof.

Computer system 900 may also include a storage device 924. Examples of a storage device (e.g., storage device 924) include, but are not limited to, a hard disk drive, a magnetic disk drive, an optical disc drive in combination with an optical medium, a solid-state memory device, and any combinations thereof. Storage device 924 may be connected to bus 912 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 924 (or one or more components thereof) may be removably interfaced with computer system 900 (e.g., via an external port connector (not shown)). Particularly, storage device 924 and an associated machine-readable medium 928 may provide nonvolatile and/or volatile storage of machine-readable instructions, data structures, program modules, and/or other data for computer system 900. In one example, software 920 may reside, completely or partially, within machine-readable medium 928. In another example, software 920 may reside, completely or partially, within processor 904.

Computer system 900 may also include an input device 932. In one example, a user of computer system 900 may enter commands and/or other information into computer system 900 via input device 932. Examples of an input device 932 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 932 may be interfaced to bus 912 via any of a variety of interfaces (not shown) including, but not limited to, a serial interface, a parallel interface, a game port, a USB interface, a FIRE-WIRE interface, a direct interface to bus 912, and any combinations thereof. Input device 932 may include a touch screen interface that may be a part of or separate from display 936, discussed further below. Input device 932 may be utilized as a user selection device for selecting one or more graphical representations in a graphical interface as described above.

A user may also input commands and/or other information to computer system 900 via storage device 924 (e.g., a removable disk drive, a flash drive, etc.) and/or network interface device 940. A network interface device, such as network interface device 940, may be utilized for connecting computer system 900 to one or more of a variety of networks, such as network 944, and one or more remote devices 948 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 944, may employ a wired and/or a wireless mode of communication. In general, any network topology may be used. Information (e.g., data, software 920, etc.) may be communicated to and/or from computer system 900 via network interface device 940.

Computer system 900 may further include a video display adapter 952 for communicating a displayable image to a display device, such as display device 936. Examples of a display device include, but are not limited to, a liquid crystal display (LCD), a cathode ray tube (CRT), a plasma display, a light emitting diode (LED) display, and any combinations thereof. Display adapter 952 and display device 936 may be utilized in combination with processor 904 to provide graphical representations of aspects of the present disclosure. In addition to a display device, computer system 900 may include one or more other peripheral output devices including, but not limited to, an audio speaker, a printer, and any combinations thereof. Such peripheral output devices may be connected to bus 912 via a peripheral interface 956. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods and apparatuses according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An apparatus for responding to a user query using a data structure, the apparatus comprising:

at least a processor; and a memory communicatively connected to the at least a processor, wherein the memory contains instructions configuring the at least a processor to:

receive a plurality of sets of note data, wherein the plurality of sets of note data comprises at least a temporal element;

analyze the plurality of sets of note data using a machine-learning module, wherein the machine-learning module comprises a large language model configured to receive the plurality of sets of note data as an input;

output, using the large language model, a cohort definition language data structure as a function of the analysis, wherein the cohort definition language data structure is output in a form of a decision tree wherein a first layer of the decision tree corresponds to a most recent timeline and subsequent layers of the decision tree reflect progressively earlier instances and wherein the cohort definition language data structure comprises a plurality of temporal criteria related to a time of treatment as nodes in the decision tree;

receive a user query datum;

generate a filtered datum as a function of the cohort definition language data structure and the user query datum wherein the filtered datum comprises a set of filtered temporal criteria related to the plurality of temporal criteria; and retrieve real-time health record data from a note database as a function of the set of filtered temporal criteria.

2. The apparatus of claim 1, wherein analyzing the plurality of sets of note data comprises analyzing the plurality of sets of note data using a Contrastive Visual Representation Learning from Text (ConVIRT) model of the machine-learning module.

3. The apparatus of claim 1, wherein analyzing the plurality of sets of note data using the machine-learning module comprises:

generating language training data, wherein the language training data comprises exemplary note data and exemplary textual outputs;

training the large language model using the language training data; and analyzing the plurality of sets of note data using the trained large language model.

4. The apparatus of claim 3, wherein analyzing the plurality of sets of note data using the machine-learning module comprises iteratively training the large language model as a function of previous iterations.

5. The apparatus of claim 3, wherein analyzing the plurality of sets of note data using the machine-learning module comprises:

generating cohort training data, wherein the cohort training data comprises correlations between exemplary note data and exemplary patient cohorts;

training a cohort classifier of the machine-learning module using the cohort training data; and classifying the plurality of sets of note data into one or more patient cohorts using trained cohort classifier.

6. The apparatus of claim 5, wherein generating the filtered datum comprises:

receiving patient data; and generating the filtered datum as a function of the patient data, the cohort definition language data structure, the user query datum, and the one or more patient cohorts.

7. The apparatus of claim 1, wherein the cohort definition language data structure comprises a JavaScript Object Notation (JSON) format.

8. The apparatus of claim 1, wherein generating the filtered datum comprises generating a subsequent filtered datum as a function of the filtered datum and a user request datum using the cohort definition language data structure.

9. The apparatus of claim 1, wherein the memory contains instructions further configuring the at least a processor to transmit the filtered datum to a remote device.

10. A method for responding to a user query using a data structure, the method comprising:

receiving, using at least a processor, a plurality of sets of note data, wherein the plurality of sets of note data comprises at least a temporal element;

analyzing, using the at least a processor, the plurality of sets of note data using a machine-learning module, wherein the machine-learning module comprises a large language model configured to receive the plurality of sets of note data as an input;

outputting, using the at least a processor and the large language model, a cohort definition language data structure as a function of the analysis, wherein the cohort definition language data structure is output in a form of a decision tree wherein a first layer of the decision tree corresponds to a most recent timeline and subsequent layers of the decision tree reflect progressively earlier instances and wherein the cohort definition language data structure comprises a plurality of temporal criteria related to a time of treatment as nodes in the decision tree;

receiving, using the at least a processor, a user query datum;

generating, using the at least a processor, a filtered datum as a function of the cohort definition language data structure and the user query datum, wherein the filtered datum comprises a set of filtered temporal criteria related to the plurality of temporal criteria; and configure the at least a processor to retrieve real-time health record data from a note database as a function of the set of filtered temporal criteria.

11. The method of claim 10, wherein analyzing the plurality of sets of note data comprises analyzing the plurality of sets of note data using a Contrastive Visual Representation Learning from Text (ConVIRT) model of the machine-learning module.

12. The method of claim 10, wherein analyzing the plurality of sets of note data using the machine-learning module comprises:

generating language training data, wherein the language training data comprises exemplary note data and exemplary textual outputs;

training the large language model using the language training data; and analyzing the plurality of sets of note data using the trained large language model.

13. The method of claim 12, wherein analyzing the plurality of sets of note data using the machine-learning module comprises iteratively training the large language model as a function of previous iterations.

14. The method of claim 12, wherein analyzing the plurality of sets of note data using the machine-learning module comprises:

generating cohort training data, wherein the cohort training data comprises correlations between exemplary note data and exemplary patient cohorts;

training a cohort classifier of the machine-learning module using the cohort training data; and classifying the plurality of sets of note data into one or more patient cohorts using trained cohort classifier.

15. The method of claim 14, wherein generating the filtered datum comprises:

receiving patient data; and generating the filtered datum as a function of the patient data, the cohort definition language data structure, the user query datum, and the one or more patient cohorts.

16. The method of claim 10, wherein the cohort definition language data structure comprises a JavaScript Object Notation (JSON) format.

17. The method of claim 10, wherein generating the filtered datum comprises generating a subsequent filtered datum as a function of the filtered datum and a user request datum using the cohort definition language data structure.

18. The method of claim 10, further comprising:

transmitting, using the at least a processor, the filtered datum to a remote device.

\* \* \* \* \*